US010912910B1

(12) United States Patent
Yezerski

(10) Patent No.: US 10,912,910 B1
(45) Date of Patent: Feb. 9, 2021

(54) COMBINATION ANESTHESIA CIRCUIT HOLDER AND PATIENT PROTECTION DEVICE AND METHOD OF USE

(71) Applicant: Tennessee Dental Anesthesia Supplies, LLC, Franklin, TN (US)

(72) Inventor: Matthew Jordan Yezerski, Franklin, TN (US)

(*) Notice: Subject to any disclaimer, the term of this patent is extended or adjusted under 35 U.S.C. 154(b) by 491 days.

(21) Appl. No.: 15/668,681

(22) Filed: Aug. 3, 2017

Related U.S. Application Data

(60) Provisional application No. 62/371,110, filed on Aug. 4, 2016.

(51) Int. Cl.
| | |
|---|---|
| *A61M 16/06* | (2006.01) |
| *A61G 13/12* | (2006.01) |
| *A61M 16/01* | (2006.01) |
| *A61M 16/00* | (2006.01) |
| *A61M 16/10* | (2006.01) |

(52) U.S. Cl.
CPC ....... *A61M 16/0683* (2013.01); *A61G 13/121* (2013.01); *A61M 16/0087* (2013.01); *A61M 16/01* (2013.01); *A61M 16/104* (2013.01)

(58) Field of Classification Search
CPC .......... A61M 16/0683; A61M 16/0497; A61M 2210/0612; A61M 2210/0687; A62B 18/084; A61F 9/04; A61F 13/124; A42B 1/006; A61B 5/6803; Y10S 2/909; Y10S 128/26; A61N 5/0621; A61G 13/121
See application file for complete search history.

(56) References Cited

U.S. PATENT DOCUMENTS

| | | | | |
|---|---|---|---|---|
| 945,839 | A * | 1/1910 | Brisbane | A61F 13/124 602/74 |
| 2,765,789 | A * | 10/1956 | Schmierer | A61F 9/0008 604/308 |
| 3,195,539 | A * | 7/1965 | Hyman | A61F 7/08 604/23 |
| 3,464,411 | A | 9/1969 | Martinez | |
| 3,541,608 | A * | 11/1970 | Otwell | A61F 9/04 2/15 |
| 3,602,227 | A | 8/1971 | Andrew | |

(Continued)

*Primary Examiner* — Kendra D Carter
*Assistant Examiner* — Victoria Murphy
(74) *Attorney, Agent, or Firm* — Lodestone Legal Group; Jeromye V. Sartain

(57) ABSTRACT

A combination anesthesia circuit holder and patient protection device apparatus configured to be worn on the head of a patient so as to cover at least the eyes and to temporarily secure an anesthesia circuit, the apparatus including a body having at least a perimeter portion and a pad configured at the perimeter portion for being positioned over the eyes of the patient, and at least two strap assemblies formed on the body, a front strap assembly positioned on a front outer surface of the body and a top strap assembly offset vertically from the front strap assembly and positioned on a top outer surface of the body, the strap assemblies cooperating to temporarily secure the anesthesia circuit, whereby placement of the apparatus on the head of the patient provides protection of at least the eyes while safely and effectively securing the anesthesia circuit in a relatively low-profile configuration with relatively minimal interference with a surgical site.

19 Claims, 9 Drawing Sheets

(56) References Cited

U.S. PATENT DOCUMENTS

| | | | | |
|---|---|---|---|---|
| 3,710,393 | A * | 1/1973 | Douglas | A61F 9/02 2/430 |
| 3,765,421 | A | 10/1973 | Poprik | |
| 3,774,616 | A | 11/1973 | White et al. | |
| 3,780,379 | A * | 12/1973 | Kampman | A61F 9/04 2/15 |
| 3,827,433 | A | 8/1974 | Shannon | |
| 4,018,221 | A * | 4/1977 | Rennie | A61M 16/0683 128/207.18 |
| 4,387,471 | A * | 6/1983 | Hsu | A41D 13/1209 128/201.12 |
| 4,502,476 | A * | 3/1985 | Welt | A61F 9/04 128/858 |
| 4,520,510 | A * | 6/1985 | Daigle | A61F 9/029 2/12 |
| 4,641,647 | A * | 2/1987 | Behan | A61M 25/02 128/207.11 |
| 4,644,588 | A * | 2/1987 | Zawacki | A61F 9/04 128/858 |
| 4,702,736 | A | 10/1987 | Kalt et al. | |
| 4,774,946 | A * | 10/1988 | Ackerman | A61M 16/0666 104/179 |
| 5,038,047 | A * | 8/1991 | Still | A61B 6/107 128/857 |
| 5,069,205 | A * | 12/1991 | Urso | A62B 18/084 128/201.24 |
| 5,244,464 | A | 9/1993 | Madden et al. | |
| 5,357,952 | A | 10/1994 | Schuster et al. | |
| 5,474,063 | A * | 12/1995 | Riendeau | A61M 16/0488 128/200.26 |
| 5,558,090 | A | 9/1996 | James | |
| 5,645,058 | A * | 7/1997 | Odom | A61M 16/0683 128/201.22 |
| 5,672,159 | A * | 9/1997 | Warrick | A61M 16/0683 128/DIG. 26 |
| 5,769,806 | A * | 6/1998 | Radow | A61F 9/04 128/858 |
| 6,088,836 | A * | 7/2000 | de Cordova | A47C 7/383 2/15 |
| 6,152,137 | A * | 11/2000 | Schwartz | A42B 1/12 128/846 |
| 6,470,886 | B1 * | 10/2002 | Jestrabek-Hart | A61M 16/0683 128/207.11 |
| 6,512,159 | B1 * | 1/2003 | Shesol | A61F 13/122 128/857 |
| 6,889,689 | B1 * | 5/2005 | Neuman | A61M 16/0683 128/201.22 |
| 7,562,658 | B2 | 7/2009 | Madaus et al. | |
| 7,748,387 | B1 * | 7/2010 | Vu | A61F 9/04 128/858 |
| 7,761,933 | B2 * | 7/2010 | Pham | A42C 1/00 2/410 |
| 7,878,968 | B2 * | 2/2011 | Wittmann-Price | A42B 1/245 600/28 |
| 7,931,023 | B2 * | 4/2011 | Berthon-Jones | A61M 16/00 128/204.21 |
| 8,025,057 | B2 | 9/2011 | Ging et al. | |
| 8,025,058 | B2 | 9/2011 | Chandran et al. | |
| 8,042,546 | B2 | 10/2011 | Gunaratnam et al. | |
| 8,096,300 | B2 | 1/2012 | Russo | |
| 8,109,271 | B2 * | 2/2012 | Vandine | A61M 16/0666 128/207.11 |
| 8,381,731 | B2 | 2/2013 | Jundt et al. | |
| 9,072,856 | B2 * | 7/2015 | Reynolds | A61M 16/0683 |
| 9,402,769 | B1 * | 8/2016 | Hudson | A61F 11/14 |
| 9,629,435 | B2 * | 4/2017 | Anderson | F21V 23/001 |
| 2002/0100475 | A1 * | 8/2002 | McKinney | A61M 16/0048 128/203.11 |
| 2003/0075174 | A1 * | 4/2003 | Shahaf | A61M 16/06 128/201.25 |
| 2004/0025884 | A1 * | 2/2004 | McKown | A61M 16/0666 128/207.18 |
| 2004/0069306 | A1 * | 4/2004 | Moenning | A61M 16/0009 128/207.13 |
| 2004/0163648 | A1 * | 8/2004 | Burton | A61M 16/0683 128/204.21 |
| 2005/0092328 | A1 * | 5/2005 | Herrick | A61M 16/0493 128/207.17 |
| 2006/0218702 | A1 * | 10/2006 | Santos | A61M 16/0683 2/422 |
| 2007/0119454 | A1 * | 5/2007 | Berthon-Jones | A61M 16/00 128/204.23 |
| 2007/0125382 | A1 * | 6/2007 | Bordier Leal | A62B 99/00 128/205.27 |
| 2007/0186931 | A1 * | 8/2007 | Zollinger | A61M 16/0683 128/207.11 |
| 2008/0047560 | A1 * | 2/2008 | Veliss | A61M 16/0605 128/206.24 |
| 2008/0060654 | A1 * | 3/2008 | Vandine | A61M 16/0683 128/207.11 |
| 2008/0092895 | A1 * | 4/2008 | Birnkrant | A61M 16/0084 128/205.13 |
| 2008/0190435 | A1 * | 8/2008 | Hansen | A61M 16/0666 128/207.18 |
| 2009/0032018 | A1 * | 2/2009 | Eaton | A61M 16/0683 128/201.22 |
| 2009/0223518 | A1 * | 9/2009 | Kwok | A61M 16/0633 128/205.25 |
| 2010/0275343 | A1 * | 11/2010 | Gibson | A61M 16/0683 2/209.13 |
| 2011/0186045 | A1 * | 8/2011 | Erickson | A61M 16/0683 128/201.23 |
| 2011/0315146 | A1 * | 12/2011 | Beevers | A61M 16/0683 128/207.13 |
| 2012/0266873 | A1 * | 10/2012 | Lalonde | A61M 16/0069 128/201.13 |
| 2013/0303837 | A1 * | 11/2013 | Berka | A61B 5/4812 600/28 |
| 2014/0158127 | A1 * | 6/2014 | Boucher | A61M 16/14 128/203.22 |
| 2014/0251342 | A1 * | 9/2014 | O'Brien | A61F 9/04 128/847 |
| 2014/0338677 | A1 * | 11/2014 | Sparkuhl | A61B 90/04 128/857 |
| 2014/0373278 | A1 * | 12/2014 | Scott | A61F 5/3707 5/640 |
| 2015/0047112 | A1 * | 2/2015 | Foster | A42B 1/18 2/422 |
| 2015/0216710 | A1 * | 8/2015 | Wanderer | A61F 5/08 128/858 |
| 2015/0238725 | A1 * | 8/2015 | Tucker | A61F 7/02 600/26 |
| 2015/0366551 | A1 * | 12/2015 | Blumenkranz | A61M 16/06 600/236 |
| 2019/0009045 | A1 * | 1/2019 | Bernard | A61M 16/0605 |

* cited by examiner

COMBINATION ANESTHESIA CIRCUIT HOLDER AND PATIENT PROTECTION DEVICE AND METHOD OF USE

RELATED APPLICATIONS

This non-provisional patent application claims priority pursuant to 35 U.S.C. § 119(e) to and is entitled to the filing date of U.S. Provisional Patent Application Ser. No. 62/371,110 filed Aug. 4, 2016, and entitled "Combination Anesthesia Circuit Holder and Patient Protection Device and Method of Use." The contents of the aforementioned application is incorporated herein by reference.

BACKGROUND

The subject of this provisional patent application relates generally to securement and patient safety devices for use during surgery, and more particularly to combination anesthesia circuit holder and patient protection devices configured for safely, comfortably, and effectively holding an anesthesia circuit or the like while also protecting the patient during oral, facial or other such surgery with minimal interference with the surgical site.

The following description includes information that may be useful in understanding the present invention. It is not an admission that any of the information provided herein is prior art or relevant to the presently claimed invention, or that any publication specifically or implicitly referenced is prior art.

Applicant hereby incorporates herein by reference any and all patents and published patent applications cited or referred to in this application, to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

By way of background, when nasal intubation or other airway management or anesthesia delivery is required for head, neck, dental or other such surgery, currently the most common approach for securing the anesthesia breathing circuit and providing any head protection is to wrap the patient's head with multiple towels using tape and then to tape the anesthesia circuit in place on the towels. This results in wasted time and supplies, with no consistency of technique between providers and with the tape sometimes becoming loose or dislodged such that the anesthesia circuit or the towel wrap can shift undesirably during the procedure. This approach is also somewhat cumbersome and generally adds unnecessary bulk and potential interference with the surgical site while not optimally protecting the patient.

Over the years, various devices have been proposed for securement of anesthesia circuits or other ventilation hoses, including nasal tracheal tubes and endotracheal tubes. Commonly these previous approaches involve adjustable or elastic straps about the head and/or neck and means for attaching the delivery hoses thereto. However, often the straps interfere with the surgical site and generally provide little to no protection of the patient's unaffected anatomy, particularly the eyes.

For example, U.S. Pat. No. 4,018,221 to Rennie issued on Apr. 19, 1977 is directed to a support for anesthetic gas delivery hoses and endotracheal tubes described as having an elongated flexible strap of predetermined width that includes opposite end portions. The strap may be encircled about a portion of a patient's body and one end of the strap includes a first fastening structure on one side thereof facing outwardly from the strap while the other end portion of the strap includes a second fastening structure on the other side thereof also facing outwardly of the strap. The first and second fastening structures are releasably engageable with each other in adjusted end overlapped positions of the opposite end portions of the strap and the second fastening structure is spaced from the corresponding terminal end of the strap with a thick, bendable and somewhat deformable but shape retentive pad being secured over and extending along the other side of the strap between the second fastening structure and the corresponding terminal end of the strap. The opposing surfaces of the pad and the portion of the strap spaced therealong toward the other end of the strap from the first fastening structure and overlapping the outer side of the pad define friction surfaces between which anesthetic gas delivery hoses may be clamped.

Other examples of delivery hose or tube securement devices that have been previously proposed include U.S. Pat. No. 4,702,736 to Kalt et al. issued on Oct. 27, 1987 and directed to a universal clamp, U.S. Pat. No. 5,244,464 to Madden et al. issued on Sep. 14, 1993 and directed to a band for securing and aligning medical tubing, U.S. Pat. No. 5,558,090 to James issued on Sep. 24, 1996 and directed to a multi-purpose head-mounted adjustable medical tube holder, U.S. Pat. No. 7,562,658 to Madaus et al. issued on Jul. 21, 2009 and directed to a holding device for a respiratory mask, and U.S. Pat. No. 8,381,731 to Jundt et al. issued on Feb. 26, 2013 and directed to a medical tubing stabilization device. Each such device, like U.S. Pat. No. 4,018,221 to Rennie, is strap-like in construction and so is relatively limited or less secure in positioning and offers effectively little to no patient protection while in some configurations still potentially interfering with the surgical field.

More recently there have been proposed strap- or hat-type securement devices in the context of continuous positive airway pressure (CPAP) ventilation equipment. One such example is found in U.S. Pat. No. 7,931,023 to Berthon-Jones et al. issued on Apr. 26, 2011 and directed to a patient interface assembly for a CPAP respiratory apparatus adapted to be connected to a gas supply pump to deliver pressurized breathable gas to the inlet of a patient's respiratory system that includes a patient interface structured to provide a seal with the patient and at least one inlet tube provided to the patient interface. Each inlet tube includes a substantially flat lower side wall to face the patient and a substantially arcuate upper side wall. Another example is U.S. Pat. No. 9,072,856 to Reynolds et al. issued on Jul. 7, 2015 and directed to a CPAP stabilizing hat having an axis of symmetry and composed of a top and sides extending down to a rim extending all around the hat. An elongated flexible panel encircles the rim. Securements secure the panel to the rim at spaced-apart locations therearound to provide a plurality of relatively long channels extending between the rim and the panel. Each channel extends parallel to the axis and is sized to slidably receive a tube. In use, a patient wears the hat and inlet and outlet tubes are retained in selected hat channels so as to stabilize a patient interface cannula connected to the tubes so that the cannula's nasal prongs remain properly positioned in the patient's nares. Though providing multiple hose attachment points, such strap or hat hose securement devices as disclosed by Berthon-Jones and Reynolds again are not configured for minimal surgical site interference or any meaningful patient protection during surgery.

What is still needed and has heretofore been unavailable is a padded head and eye protection device to be worn by a patient that also provides relatively low profile anesthesia circuit retention so as to eliminate unnecessary obstruction of the surgical field. Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing a combination anesthesia circuit holder and patient protection device configured in various embodiments and according to aspects thereof for safely, comfortably, and effectively holding an anesthesia circuit or the like while also protecting the patient during oral, facial or other such surgery with relatively minimal interference with the surgical site. In at least one embodiment, the device comprises a body formed as a hat or pad sized and configured to be placed on a patient's head and over the eyes and having one or more strap assemblies situated on the front, sides and/or top portion(s) of the body for further protection of the patient while securing an anesthesia circuit during use.

Other objects, features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

Figure 1:
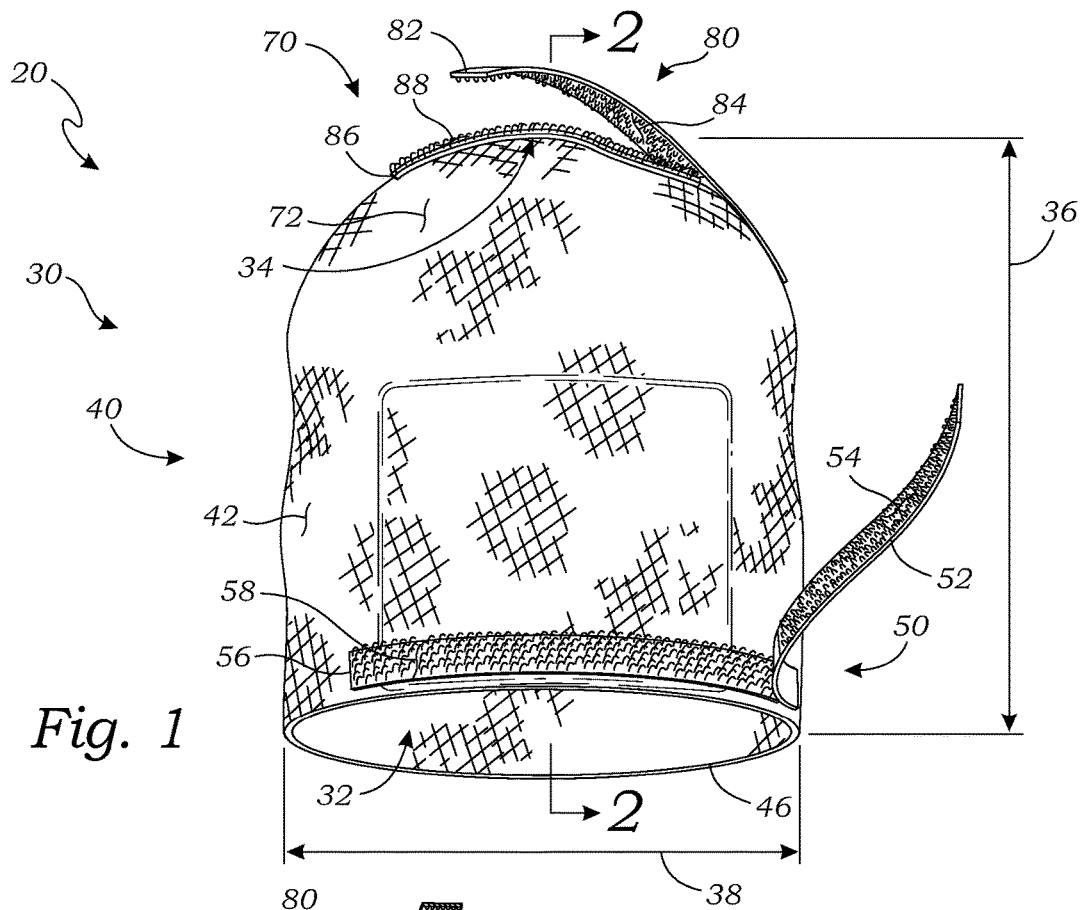
FIG. 1 is a perspective view of an exemplary anesthesia circuit holder and patient protection device, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments. More generally, those skilled in the art will appreciate that the drawings are schematic in nature and are not to be taken literally or to scale in terms of material configurations, sizes, thicknesses, and other attributes of an apparatus according to aspects of the present invention and its components or features unless specifically set forth herein.

DETAILED DESCRIPTION

The following discussion provides many exemplary embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

While the inventive subject matter is susceptible of various modifications and alternative embodiments, certain illustrated embodiments thereof are shown in the drawings and will be described below in detail. It should be understood, however, that there is no intention to limit the invention to any specific form disclosed, but on the contrary, the inventive subject matter is to cover all modifications, alternative embodiments, and equivalents falling within the scope of the claims.

Turning first to FIG. 1, there is shown a perspective view of an exemplary embodiment of a combination anesthesia circuit holder and patient protection device 20 according to aspects of the present invention. As a threshold matter, "anesthesia circuit," "anesthesia breathing circuit" or "breathing circuit" or other such terms are to be understood broadly as any hoses, tubes or other such conduits and/or fittings now known or later developed for delivery of gases to a patient's airway, whether through the mouth and/or the nose, such that the invention is not limited to the exemplary anesthesia circuits shown and described herein. The device 20 comprises, in the exemplary embodiment, a body 30 formed as a hat with an opening 32 sized and configured for receipt of a patient's head H (FIGS. 3 and 4) and having a perimeter portion 40 and a top portion 70 and further having at least one strap assembly 50, 80. As a further threshold matter, it will be appreciated that while a hat configuration is shown in the first exemplary embodiment, the invention is not so limited, but may take other forms, as will be further appreciated with reference to the full and partial pad configurations of the device 20 shown and described in connection with FIGS. 10-15 below. In the illustrated embodiment, two strap assemblies 50, 80 are employed: a first or front strap assembly 50 positioned on the front of the perimeter portion 40 of the body 30 in the vicinity of an incorporated pad 90 and a second or top strap assembly 80 positioned on the top portion 70 of the body 30, more about which is said below. The hat-like body 30 may be formed of any suitable material now known or later developed having the desired comfort, elasticity/stretchability, and/or breathability, including but not limited to cotton, polyester, nylon, spandex/elastane, or any blends thereof. The hat-like body 30 may also be formed from any suitable manufacturing process now known or later developed, whether as a unitary construction woven, knit, or otherwise formed from a single piece of fabric or as any combination of panels stitched or otherwise joined together, including but not limited to any reinforcing panels at the opening 32 of the body 30 or in conjunction with the attachment of the strap assemblies 50, 80, for example, or as in the alternative embodiment of FIGS. 8 and 9 wherein side inserts 120 are formed on opposite sides of the perimeter portion 40 of the body 30 to provide breathability and comfort and potentially other properties such as elasticity, more about which is said below. In any event, the device 20 may be a multiple-use product in which case wear and washability and other factors may be taken into account in material and construction methodology selection or may be a single-use or disposable product for which material and construction cost relative to performance would be further considered along with environmental impact and other factors. It will be appreciated by those skilled in the art that a variety of other configurations of the hat-like device 20 and its material(s) and method(s) of construction are possible according to aspects of the present invention without departing from its spirit and scope, such that the illustrated device 20 is to be understood as exemplary and non-limiting. Generally, the drawings are schematic in nature and are not to be taken literally or to scale in terms of material configurations, thicknesses, and other attributes of the device 20 and its components or features unless specifically set forth herein.

Figure 3:
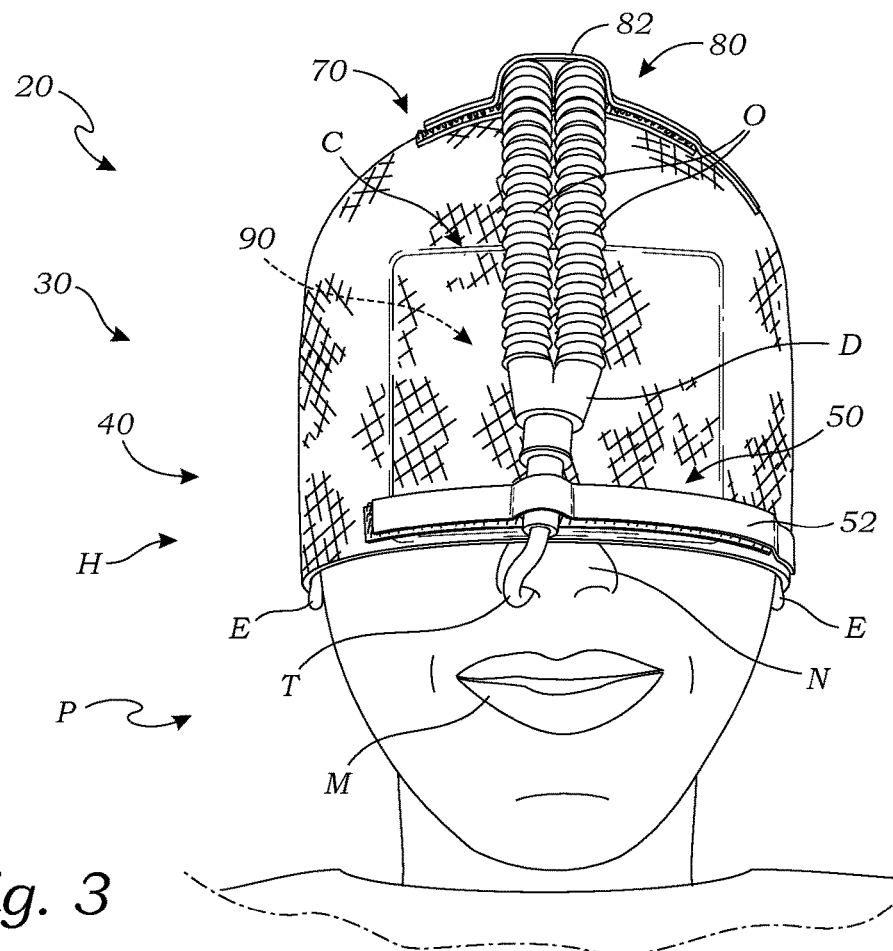
FIG. 3 is a front perspective view thereof in use, in accordance with at least one embodiment.
Figure 4:
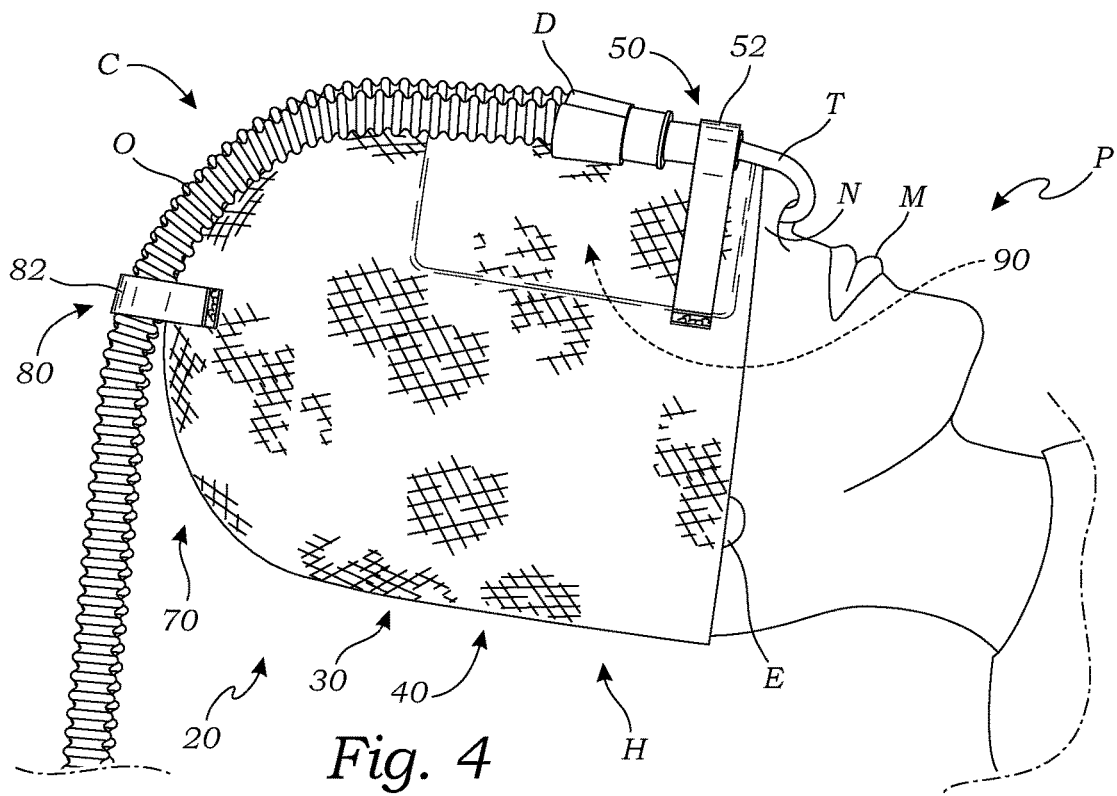
FIG. 4 is a side perspective view thereof in use, in accordance with at least one embodiment.

Dimensionally, those skilled in the art will appreciate that the combination anesthesia circuit holder and patient protection device 20 according to aspects of the present invention may vary widely in size and shape depending on a number of factors and intended uses. Any particular configuration of the device 20 may simply be scaled up or down to suit particular contexts or patients, such as adult and pediatric versions, for example. More generally, it will be appreciated that the average adult head circumference is in the range of twenty to twenty-five inches (20-25 in.) while for children it is in the range of eighteen to twenty-two inches (18-22 in.), which translates to diameters nominally ranging from approximately six to eight inches (6-8 in.) for adult head or hat sizes and from approximately five-and-a-half to seven inches (5.5-7 in.) for children. Accordingly, the hat-like body 30 may be configured having a nominal opening 32, for example, of seven-inch (7 in.) diameter for adults and six-inch (6 in.) diameter for pediatric. However, it will be appreciated that with a sufficiently elastic or stretchy material, the body 30, and body opening 32 specifically, may be sized at the low end of a particular range or below to accommodate head sizes above, or effectively provide a "one size fits all" device 20. Relatedly, those skilled in the art will appreciate that with particularly elastic or stretchy materials of construction, the nominal or "at rest" or "unworn" size of the device 20 may be below the relevant head size range allowing for all such variance to be taken up by the material and for a sufficiently snug fit of the device 20 for all patients. Again, those skilled in the art will appreciate that a variety of configurations and materials of construction and thus dimensional sizes may be employed in the device 20 according to aspects of the present invention. More significantly, in the interest of the device 20 performing a patient safety function, or protecting the patient and particularly the eyes, bridge of the nose, ears, and portions of the face and head more generally during surgery, it is desirable that the length or height 36 of the body 30 of the device 20 be sufficiently proportioned relative to its nominal diameter or width 38 so as to be able to be comfortably pulled down over the eyes and ears of the patient P during use as illustrated in FIGS. 3 and 4, discussed further below. Therefore, a dimensional characteristic according to aspects of the device 20 of the present invention is that the nominal height 36 of the body 30 as measured from the opening 32 to the opposite apex 34 is as great or greater than the nominal width 38 of the body 30 as measured across the body side portion 40 effectively at the opening 32. In a bit more detail, with reference to Table 1 below (measurements 9 and 10, taken from en.wikipedia.org/wiki/Human_head on Jul. 27, 2016), in male and female adult heads, the average vertical distance from the nasal root depression between the eyes (sellion) to the top of the head is in the range of four to four-and-a-half inches (4-4.5 in.) and the average vertical distance from the midpoint of the lips (stomion) to the top of the head is in the range of seven to seven-and-a-half inches (7-7.5 in.). Taking the midpoint therebetween to be an intermediate location along the nose below the bridge of the nose and the eyes, it follows that a vertical distance from such location to the top of the head is in the range of five-and-a-half to six inches (5.5-6 in.) in the average adult. However, allowing for the patient's hair and for more circumferential stretch being permissible or expected than axial stretch in the body 30 during use, it follows that an approximate height 36 of the body 30 would be on the order of seven to nine inches (7-9 in.) or greater as compared with the nominal width 38 of the body 30 of on the order of six to eight inches (6-8 in.) or less for average adult head size. Again, those skilled in the art will appreciate that a variety of other dimensions are possible depending on a number of factors, including but not limited to the intended use and material(s) of construction of the device 20, such that the indicated dimensions are to be understood as illustrative and non-limiting. For example, in alternate embodiments, the nominal height 36 of the body 30 as measured from the opening 32 to the opposite apex 34 may be less than the nominal width 38 of the body 30 as measured across the body side portion 40 effectively at the opening 32, even if slightly. Regardless, aspects of the present invention are thus directed to a device 20 having a body 30 configured to substantially enclose and protect the perimeter and top of a patient's head and provide one or more securement points at such perimeter and/or top locations while having sufficient size or length to also cover and protect the patient's eyes and ears. As such, and by way of further illustration and not limitation, the body 30 of the device 20 according to aspects of the present invention may be characterized as having a nominal height 36 relative to or as a percentage of its nominal width 38 of at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, or more.

TABLE 1

Head Anthropometry, sellion and stomion height measurements

Sellion to top of head. The vertical distance from the nasal root depression between theeyes (sellion) to the level of the top of the head, measured with a headboard.

| Sample | | | 1st | 5th | 50th | 95th | 99th |
|---|---|---|---|---|---|---|---|
| | | | | | Percentiles | | |
| A | Men | cm | 9.7 | 10.1 | 11.2 | 12.4 | 12.9 |
| | | in | 3.8 | 4.0 | 4.4 | 4.9 | 5.1 |
| B | Women | cm | 9.0 | 9.5 | 10.5 | 11.7 | 12.2 |
| | | in | 3.5 | 3.7 | 4.1 | 4.6 | 4.8 |

Stomion to top of head. The vertical distance from the midpoint of the lips (stomion) to the level of the top of the head, measured with a headboard.

| Sample | | | 1st | 5th | 50th | 95th | 99th |
|---|---|---|---|---|---|---|---|
| | | | | | Percentiles | | |
| A | Men | cm | 16.9 | 17.4 | 18.6 | 19.9 | 20.6 |
| | | in | 6.7 | 6.9 | 7.3 | 7.8 | 8.1 |
| B | Women | cm | 15.7 | 16.3 | 17.5 | 18.8 | 19.4 |
| | | in | 6.1 | 6.4 | 6.9 | 7.4 | 7.6 |

With continued reference to FIG. 1, there is again shown a body 30 formed as a hat having a perimeter portion 40 with a first or front strap assembly 50 and a top portion 70 with a second or top strap assembly 80. Each such strap assembly 50, 80 may be formed of any suitable removably engageable materials, fasteners, or the like now known or later developed, including but not limited to hook-and-loop fasteners, adhesives, snaps, buttons, zippers, buckles, and clips. In the illustrated embodiment, the strap assemblies 50, 80 each comprise hook-and-look fastener strap portions 52, 56, 82, 86. In more detail, taking first the front strap assembly 50, a selectively movable or repositionable front first strap portion 52 is installed on the perimeter portion 40 so as to be staked at one end only, with the remainder of the front first strap portion 52 to its opposite end being free or un-staked and having an inwardly-facing front first fastener portion 54. A front second strap portion 56 is installed on the perimeter portion 40 so as to underlie or extend in the same direction as the front first strap portion 52, only the front second strap portion 56 is staked along its full length to the underlying perimeter portion outer surface 42 and has on its opposite side a front second fastener portion 58 configured to face and selectively engage with the front first fastener portion 54 of the front first strap portion 52. As illustrated, the front second fastener portion 58 contains the "hooks" and the front first fastener portion 54 contains the "loops" of the typical hook-and-loop fastener, though it will of course be appreciated that this could be reversed. In the illustrated embodiment, both the front first and second strap portions 52, 56, and hence the front strap assembly 50 itself, are positioned substantially parallel and adjacent to the lower perimeter edge 46 of the perimeter portion 40 of the body 30 of the device 20, essentially centered on what amounts to the "front" of the device 20 when worn as being co-located about the circumference of the body 30 with the pad 90, more about which is said below in connection with FIG. 2 regarding the pad 90 and with FIGS. 3 and 4 regarding the device 20 in use. Similarly, with continued reference to FIG. 1, regarding the top strap assembly 80, a selectively movable or repositionable top first strap portion 82 is installed on the top portion 70 so as to be staked at one end only, with the remainder of the top first strap portion 82 to its opposite end being free or un-staked and having an inwardly-facing top first fastener portion 84. A top second strap portion 86 is installed on the top portion 70 so as to underlie or extend in the same direction as the top first strap portion 82, only the top second strap portion 86 is staked along its full length to the underlying top portion outer surface 72 and has on its opposite side a top second fastener portion 88 configured to face and selectively engage with the top first fastener portion 84 of the top first strap portion 82. As again illustrated, the top second fastener portion 88 contains the "hooks" and the top first fastener portion 84 contains the "loops" of the typical hook-and-loop fastener, though it will once more be appreciated that this could be reversed. It will also be appreciated that one or more strap assembly may comprise one type of fastener and one or more another and that the strap assemblies 50, 80 need not necessarily be oriented the same way or have their first strap portions 52, 82 staked on the same side or in the same way. It will thus be appreciated that a wide variety of locations and means of installation for such one or more strap assemblies is possible according to aspects of the present invention without departing from its spirit and scope. In the illustrated embodiment, both the top first and second strap portions 82, 86, and hence the top strap assembly 80 itself, are positioned substantially parallel to the front strap assembly 50 and thus the lower perimeter edge 46, here spaced from the front strap assembly 50 and essentially centered on and passing over the apex 34 of the top portion 70 of the body 30 of the device 20. Again, those skilled in the art will appreciate that variations in the number, placement, and configuration of such one or more strap assemblies may be employed according to aspects of the present invention, such that the illustrated two strap assemblies 50, 80 are to be understood as exemplary and non-limiting. Such strap assemblies 50, 80, and the strap and fastener portions thereof, may be formed from any suitable material and process now known or later developed, including but not limited to nylon, polypropylene, polyester, cotton, spandex/elastane, or any blends thereof so as to form a webbing material, whether inelastic or elastic as desired. Such strap assemblies 50, 80 may be installed, in whole or in part, on the body 30 of the device 20 employing any suitable technique now known or later developed, including but not limited to stitching, bonding, welding, or adhesives. Dimensionally, the length and width of each of the strap assemblies 50, 80 may vary widely to suit particular applications or intended uses and other factors. By way of illustration and not limitation, each strap assembly 50, 80, and particularly one or more of the strap portions 52, 56, 82, 86, may be sized and configured to span more than half of the width 38 of the body 30, those skilled in the art appreciating that based on such size and configuration or variable fastening or closure capability of the strap assemblies 50, 80, the resulting device 20 would be capable of securing a variety of hoses, anesthesia circuits, delivery lines and the like, both in size and configuration and in position relative to the device 20 (e.g., going straight over the top of the device 20 versus off-center). In the illustrated embodiment, each of the strap portions 52, 56, 82, 86 is in the range of one-half to three inches (0.5-3 in.) in width, and the length of particularly the affixed second strap portions 56, 86 is in the range of three to seven inches (3-7 in.), it being appreciated that the selectively closable, partially anchored first strap portions 52, 82 would be proportionately longer both due to their attachment to the body 30 offset from the second strap portions 56, 86 so as to align the respective fastener portions 54, 58, 84, 88 and to allow for closure around the selected hose(s) or line(s) of an anesthesia circuit C (FIGS.

3 and 4) or the like, which would add further bulk to be encompassed effectively by the first strap portions 52, 82. Once more, those skilled in the art will appreciate that the number, configuration and placement of any such strap assemblies 50, 80 may vary from those shown and described according to aspects of the present invention without departing from its spirit and scope.

Figure 2:
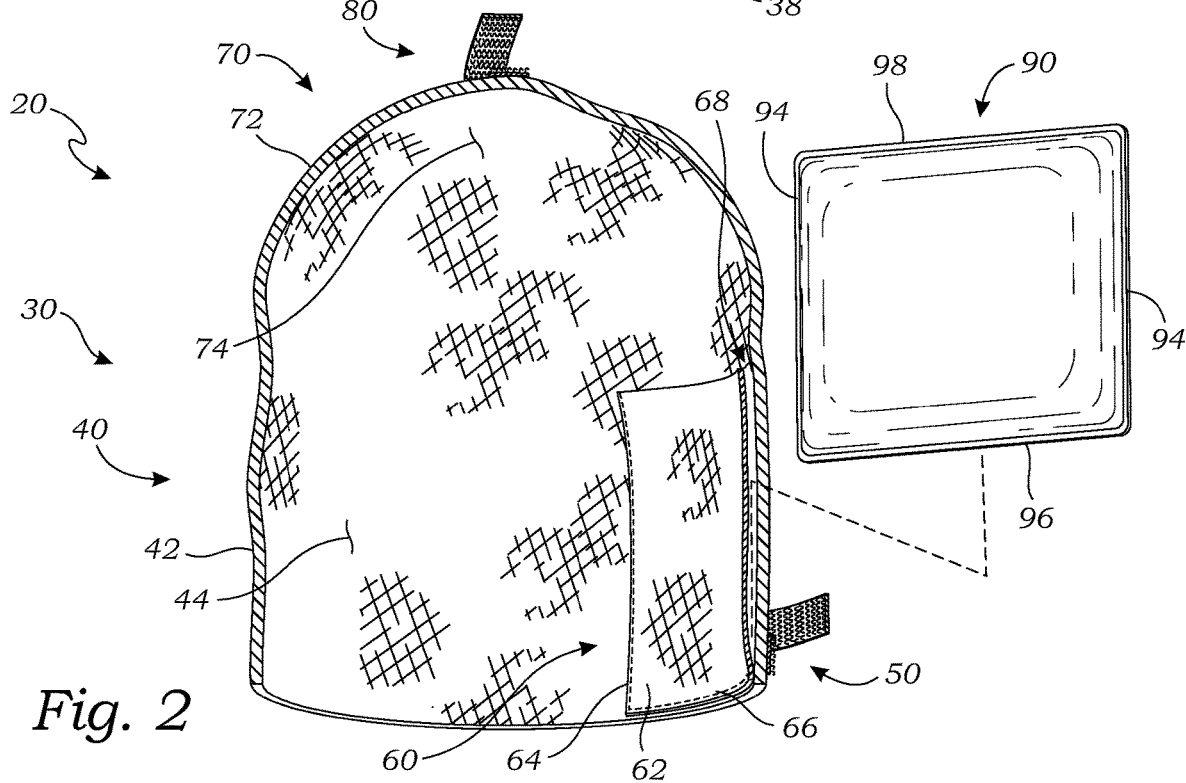
FIG. 2 is a side cross-sectional view thereof, in accordance with at least one embodiment.

Turning to FIG. 2, there is shown a cross-sectional view of the exemplary combination anesthesia circuit holder and patient protection device 20 of FIG. 1 taken along line 2-2. The device 20 once again comprises in the illustrated embodiment a body 30 formed as a hat having a perimeter portion 40 with a front strap assembly 50 and a top portion 70 with a top strap assembly 80. Notably, as best seen in FIG. 2, the device 20 further comprises a pad 90 located toward its lower front so as to provide additional comfort and protection to the patient during use. In one embodiment, as shown, the pad 90 is removable, as being selectively removably received within an appropriately sized and configured pocket 60 formed within the body 30. Alternatively, the pad 90 may be integral with the body 30, as either being separately formed and permanently secured to the body 30 or in the body 30 or a pocket 60 thereof or being itself formed integral with the body 30, such as by being knitted, woven, stitched, etc. as part of the body 30, and the side portion 40 specifically. Where the pad 90 is to be separately formed and received in a pocket 60, whether removably or permanently, it will be appreciated that the dimensions (size and shape) of both the pocket 60 and pad 90 should be so configured as to accommodate one another. In the illustrated embodiment, there is formed within the body 30 as being affixed to the inner surface 44 of the side portion 40 a pocket 60 having an opening 68 at the top for receipt of the pad 90. More particularly, the pocket 60 comprises a panel 62 made of any appropriate material now known or later developed, including but not limited to cotton, polyester, nylon, spandex/elastane, or any blends thereof, preferably in at least one embodiment such material being the same as that forming the body 30, the panel 62 having side attachment points or seams 64 and a bottom attachment point or seam 66, again leaving the top of the pocket 60 unattached or open, thus defining the opening 68 opposite the bottom seam 66. It will be appreciated that such opening 68 may be selectively closed as by forming the pocket 60 at its upper end adjacent the opening 68 with a top flap or other closure means (not shown) now known or later developed, including but not limited to hook-and-loop fasteners, adhesives, snaps, buttons, zippers, buckles, and clips, though in certain contexts and embodiments any such closure means would not be employed, the pad 90 being sufficiently retained by friction and/or the orientation of the pocket 60 relative to the patient. Those skilled in the art will also appreciate that the pocket 60 may be formed in alternate locations on the outside or inside of the body 30 and in alternate orientations, particularly as to any opening 68, such that the exemplary embodiment shown and described is to be understood as illustrative and non-limiting. It will be appreciated that where the pocket 60 is internal and the opening 68 is toward the top, the body 30 may simply be turned inside-out for easier access to the pocket 60 and the pad 90. Where the pad 90 is removable, those skilled in the art will appreciate that cleaning of both the body 30 and the pad 90 and replacement of the pad 90 is facilitated. Regardless, as shown, the pocket 60 is preferably located near or adjacent to the lower perimeter edge 46 of the perimeter portion 40 of the body 30 so as to ultimately position the pad 90 housed within the pocket 60 relatively lower and nearer to the patient's nose, eyes and upper face anatomy generally, again for protection during any surgical procedure the patient is undergoing and further for comfort even relative to the anesthesia circuit C or other hoses or the like that are temporarily secured to the device 20, typically passing across or over the patient's face along or on either side of the nose N, more about which is said below in connection with FIGS. 3 and 4 and the device 20 in use. With continued reference to FIG. 2, the pad 90 is here shown as being substantially square, though it will be appreciated that it can be formed of virtually any size or shape. In the exemplary embodiment the shape of the pad 90 substantially conforms to that of the pocket 60, with the side edges 94 of the pad 90 corresponding to the pocket's side seams 64, the pad's bottom edge 96 corresponding to the pocket's bottom seam 66, and the pad's top edge 98 corresponding to the pocket's opening 68. Though not shown, the removable pad 90 may be further formed with a handle or other feature to facilitate insertion within and removal from the pocket 60. In any case, the pad 90 may be formed of any pliable, conformable material now known or later developed suitable for absorbing momentary or continuous forces or loads, as again may be applied thereto ranging from a dropped instrument to a practitioner's arm to the temporarily secured anesthesia circuit C, for example. The pad 90, just as the overall device 20 or the body 30 thereof, may be reusable or "single use" and configured accordingly. Again any suitable material or method of production now known or later developed may be employed, including but not limited to woven or knitted fabrics or textiles, foams, rubbers, or any combinations thereof. Preferably any such material would be selected to provide the desired padding (comfort and protection) with minimal thickness so as to assist in maintaining an overall low profile of the device 20 and related anesthesia circuit C or other apparatus secured thereon during use, more about which is said below. Dimensionally, once again, both the pad 90 and any pocket 60 in which it is placed preferably are located in the lower front region of the body 30 of the device 20 and so may be sized and configured to span the anatomy over which that region of the device 20 is to be positioned during use, particularly so as to cover and further protect the eyes, bridge of the nose, cheeks and/or forehead. Those skilled in the art will appreciate that the pad 90 may be sized and shaped to cover more or less of such anatomy depending on a number of factors. In the exemplary embodiment, and for illustration and not limitation, the pad 90 may nominally be in the range of four to eight inches (4-8 in.) on a side or even square. More specifically, it is noted with reference to Table 2 below (measurements 5 and 6, taken from en.wikipedia.org/wiki/Human_head on Jul. 27, 2016) that in adults the average biocular breadth, or the distance from the outer corners of the eyes, is in the range of four to five inches (4-5 in.) and the average bitragion breadth from the right tragion to the left (or essentially between the outer ear notches) is in the range of five to six inches (5-6 in.). Accordingly, in average adult patients, the width of the pad 90, or the distance between opposite side edges 94, is preferably in the range of at least four to six inches (4-6 in.). Similarly, with reference to Table 1 above and being reminded that the average vertical distance in adults from an intermediate location along the nose below the bridge of the nose and the eyes to the top of the head is in the range of five-and-a-half to six inches (5.5-6 in.), it follows that the height of the pad 90, or the distance between the bottom and top edges 96, 98, is preferably in the range of five to six inches (5-6 in.) or more. Accordingly, an overall pad dimension of at least on the order of five inches (5 in.) on a side or square would afford protection and additional comfort for most patients. Preferably the pad 90 is no thicker than one inch (1 in.), though in certain applications thicker pads may be tolerated or even preferred. Once more, those skilled in the art will appreciate that smaller and certainly larger pads 90 may be employed without departing from the spirit and scope of the invention.

TABLE 2

Head Anthropometry, biocular and bitragion breadth measurements

Biocular breadth. The distance from the outer corners of the eyes (right and left ectocanghti).

| Sample | | | Percentiles | | | | |
|---|---|---|---|---|---|---|---|
| | | | 1st | 5th | 50th | 95th | 99th |
| A | Men | cm | 11.0 | 11.3 | 12.2 | 13.1 | 13.6 |
| | | in | 4.3 | 4.5 | 4.8 | 5.2 | 5.4 |
| B | Women | cm | 10.8 | 11.1 | 11.6 | 12.9 | 13.3 |
| | | in | 4.3 | 4.4 | 4.6 | 5.1 | 5.3 |

Bitragion breadth. The breadth of the head from the right tragion to the left (tragion is the cartilaginous notch at the front of the ear).

| Sample | | | Percentiles | | | | |
|---|---|---|---|---|---|---|---|
| | | | 1st | 5th | 50th | 95th | 99th |
| A | Men | cm | 13.1 | 13.5 | 14.5 | 15.5 | 15.9 |
| | | in | 5.2 | 5.3 | 5.7 | 6.1 | 6.3 |
| B | Women | cm | 12.5 | 12.8 | 13.3 | 14.3 | 15.0 |
| | | in | 4.9 | 5.0 | 5.2 | 5.6 | 5.9 |

Referring now to FIGS. 3 and 4, there are shown front and side perspective views of the exemplary combination anesthesia circuit holder and patient protection device 20 of FIGS. 1 and 2 as now in use on a patient P. As shown, the device 20, and particularly the body 30 thereof, may be pulled over the head H of the patient P until fully seated, positioning the body 30, and specifically the side portion 40 thereof, over the eyes (not shown), all or part of the ears E, and most of the nose N, particularly the bridge of the nose (not shown) between the eyes, as the top portion 70 of the body 30 substantially contacts the area of the crown of the head H. As such, the entire head H of the patient P is substantially covered and protected by the device 20 from the ears E up while leaving exposed the nostrils of the nose N for intubation purposes and the mouth M and jaw area for access in the event of oral of facial surgery. With the device 20 so positioned on the head H, the patient P may be intubated in any clinically appropriate manner now known or later developed in the art for purposes of airway maintenance or ventilation and/or anesthesia delivery. As illustrated, a conventional anesthesia circuit C is employed along with a nasal tracheal tube T connected via a connector D, here teeing to two hoses O, one for delivery (inhalation) and the other for return (exhalation). The tube T is inserted into the patient's nose N (here, one of two nostrils) and brought up and over the patient's nose and face where it is again connected to the circuit C via connector D. In the exemplary use, the complete circuit assembly is then secured and held in position as by removably engaging the strap assemblies 50, 80 thereover—here, the lower or front strap assembly 50 engaging the connector D and/or tube T and the upper or top strap assembly 80 engaging the circuit C, and particularly the pair of parallel hoses O. Those skilled in the art will appreciate that the first strap portions 52, 82 of the respective strap assemblies 50, 80 may be pulled and tightened down sufficiently to immobilize the overall circuit C and thereby prevent movement of the tube T relative to the patient's nose N or the circuit hoses H relative to the device body 30. It will be further appreciated that even the texture of the exemplary hook-and-loop fastener portions 54, 58, 84, 88 (FIG. 1) provides frictional engagement with the circuit components, further securing the circuit C and tube T relative to the patient P and the device 20 and thus preventing unwanted movement or displacement. Relatedly, it will be appreciated that by securing the circuit C at two points, particularly two points that are out of plane relative to each other, movement of the circuit C relative to the device 20 is further prevented. Accordingly, while one securement location is possible, multiple securement locations is preferable. Thus, while two securement locations (strap assemblies 50, 80) are shown and described, three or more such strap assemblies or other such securement devices may be employed without departing from the spirit and scope of the invention, again, whether the same or different or in-line or off-line relative to each other. Moreover, by snugging the circuit C down over or onto the device 20, those skilled in the art will appreciate that a low profile is maintained with the circuit 30 substantially clear of and not interfering with or obstructing the surgical field. Such "snugging down" is tolerated or assisted due to the incorporation of the pad 90, particularly for the more sensitive areas of the face over which the pad 90 and lower front strap assembly 50 are positioned. While the anesthesia circuit C is shown particularly in FIG. 3 from the front as being substantially centered on the patient's head H, or passing directly over the nose N between the eyes (not shown), it will be appreciated that the circuit C can instead be shifted to one side or the other and that the configuration and placement of the strap assemblies 50, 80 facilitate such variations in securement position. Clinically, it may be desirable to shift the circuit C to one side or the other depending on a number of factors, including but not limited to the patient's anatomy, the location of the surgical site, and the intubation method. Once more, strap assemblies 50, 80 according to aspects of the present invention may be adapted to such varied clinical uses. In any event, the relatively tight fitting and low profile configuration of the device 20, including the pad 90, further facilitates securing the anesthesia circuit C or other apparatus in an unobtrusive manner so as to minimize interference with the surgical site.

Figure 5:
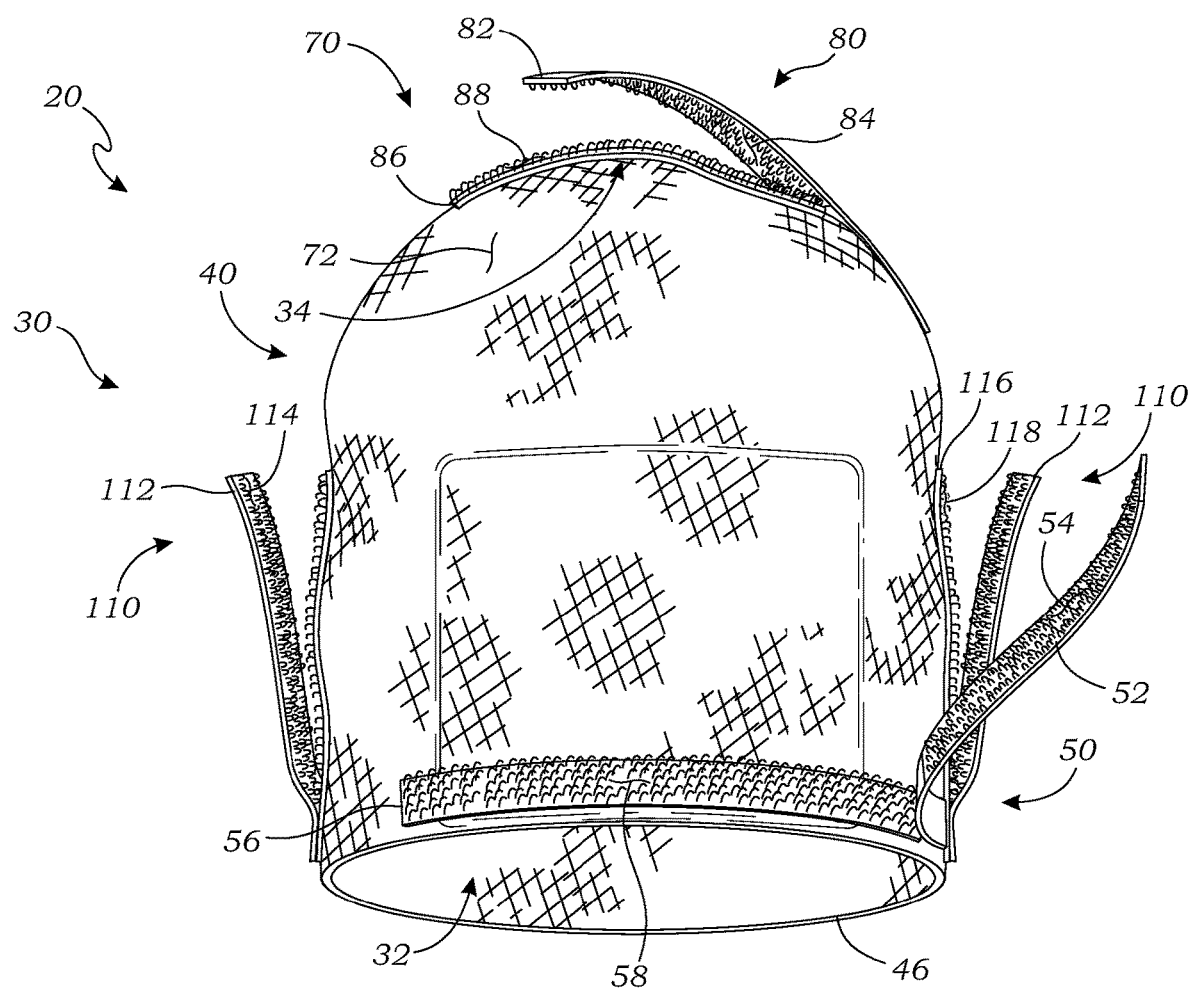
FIG. 5 is a perspective view of an alternative exemplary anesthesia circuit holder and patient protection device, in accordance with at least one embodiment.
Figure 6:
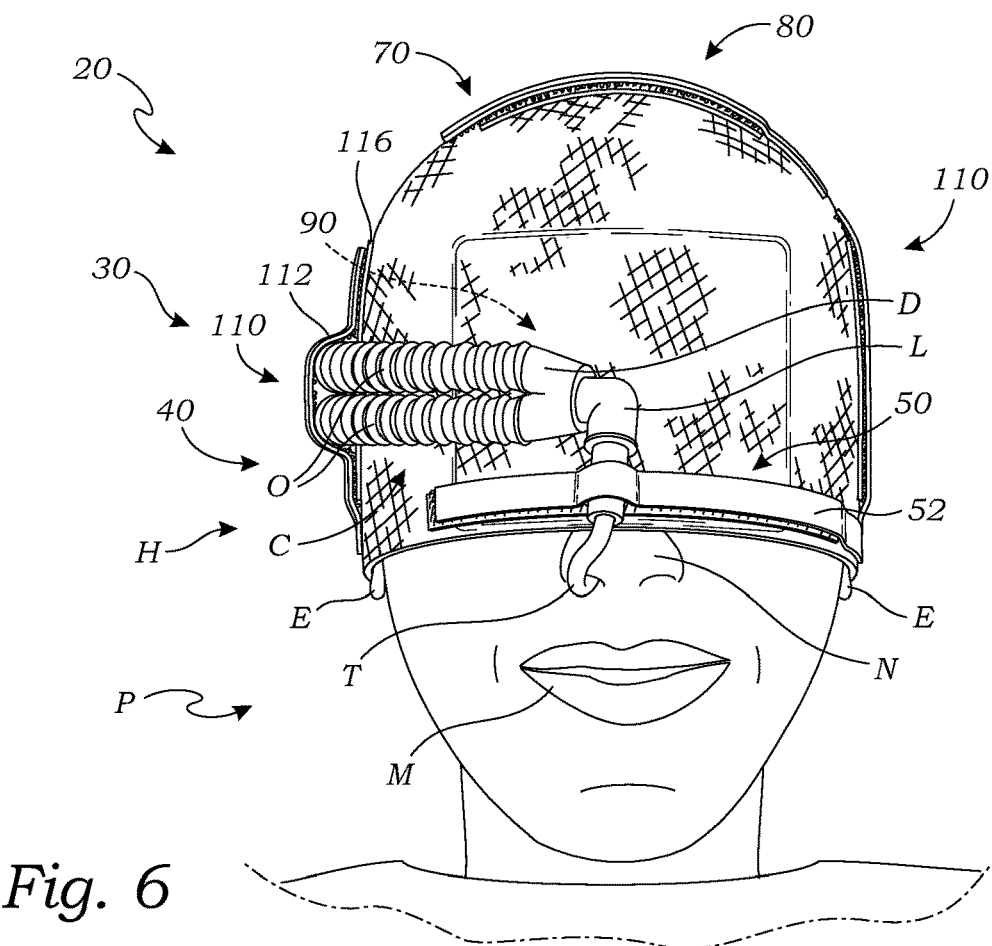
FIG. 6 is a front perspective view thereof in use, in accordance with at least one embodiment.
Figure 7:
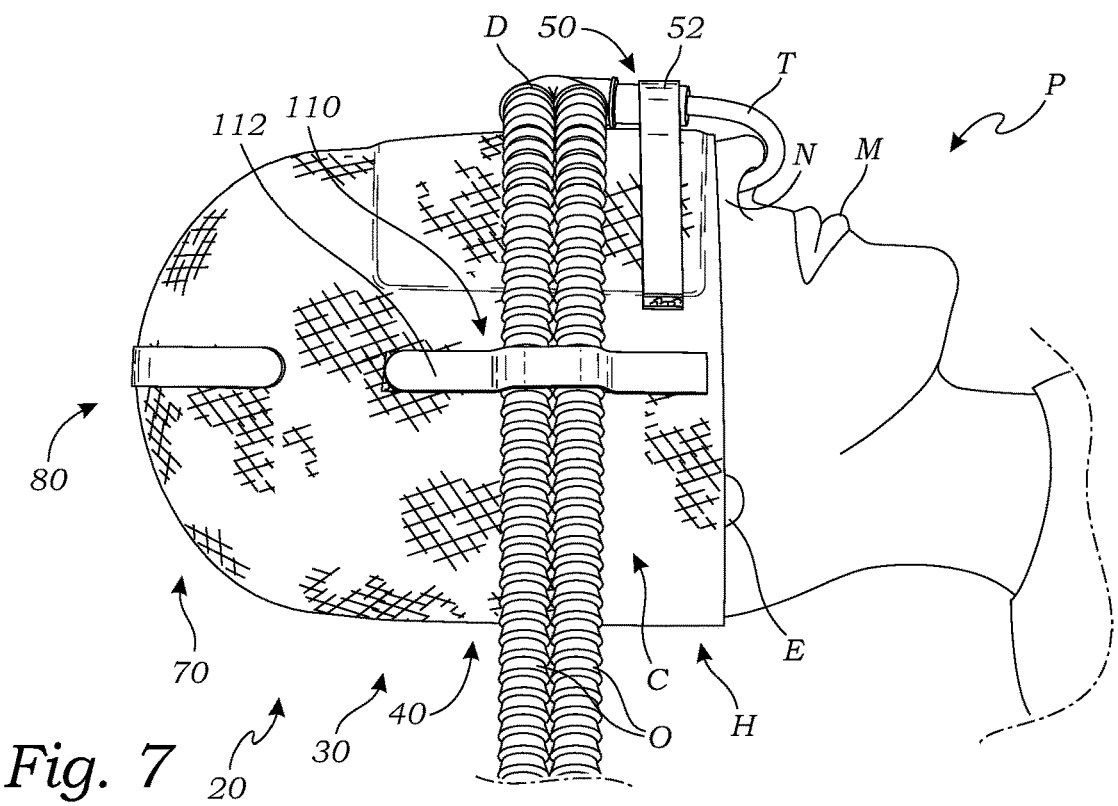
FIG. 7 is a side perspective view thereof in use, in accordance with at least one embodiment.

Turning next to FIGS. 5-7, there is shown an alternative exemplary embodiment of a combination anesthesia circuit holder and patient protection device 20 according to aspects of the present invention, here in many respects being analogous to the hat-like embodiment of FIGS. 1-4, only now providing opposite side strap assemblies 110 similar to the front and top strap assemblies 50, 80 but here positioned on the sides of the perimeter portion 40 of the body 30 of the device 20 and oriented somewhat perpendicular to the front strap assembly 50. As in other embodiments disclosed herein, each side strap assembly 110 is shown as comprising a selectively movable or repositionable side first strap portion 112 installed on the perimeter portion 40 so as to be staked at one end only, with the remainder of the side first strap portion 112 to its opposite end being free or un-staked and having an inwardly-facing side first fastener portion 114 and further comprising a side second strap portion 116 installed as staked along its full length on the perimeter portion 40 so as to underlie or extend in the same direction as the side first strap portion 112 with its side second fastener portion 58 configured to face and selectively engage with the side first fastener portion 114 of the side first strap portion 112. Once more, which strap portion 112, 116 contains the "hooks" and which the "loops" of the typical hook-and-loop fastener does not matter, and any such temporary or repositionable fastening means now known or later developed may be employed. In use, the device 20 is placed over the head H of the patient P so as to substantially cover and protect the eyes (not shown) and bridge of the nose N area as herein described. When a circuit C is employed having an elbow L between the tube T and the connector D as may sometimes be the case, having such side strap assemblies 110 facilitates securement of the circuit C around the side of the patient's head H rather than over the top so as to again maintain a low profile and minimize obstruction of the surgical site and surrounding field. That is, with the circuit C having a ninety-degree elbow L, rather than taking the circuit C, and circuit hoses O specifically, over the top of the head H, which it will be appreciated would require a much greater stand-off of the circuit C from the head H in the area of the connector D, typically addressed in practice through stacking gauze, towels, or other filler material on the patient's head H beneath the connector D, the elbow L is allowed to rotate to either side and lay flat across the head H, directing the hoses O around a side of the head H, again, rather than over the top of the head H. Accordingly and conveniently, by providing the device 20, with the opposite side strap assemblies 110, such circuit hoses O can be routed to either side of the head H at the clinician's election, with the outer side first strap portion 112 of the involved side strap assembly 110 fastened to the underlying inner side second strap portion 116 over and about the hoses O to secure them in place as shown in FIGS. 6 and 7, the other side strap assembly 110 not employed as well as the top strap assembly 80 may simply be secured flat and out of the way. As shown, the tube T itself is still secured within the front strap assembly 50 as previously described. In this way, those skilled in the art will appreciate that by providing a combination anesthesia circuit holder and patient protection device 20 according to aspects of the present invention with not only front and top strap assemblies 50, 80 but also one or more side strap assemblies 110 a range of circuits C or circuit arrangements with various connectors D and/or elbows L may be accommodated in still temporarily securing such circuits C relatively flush or in a low-profile manner as illustrated. It will be further appreciated once more that a variety of other configurations of such a device 20 employing various combinations of components and features as herein described and as now known or later developed may be practiced according to aspects of the present invention without departing from its spirit and scope, such that the exemplary embodiments are to be understood as illustrative and non-limiting.

Figure 8:
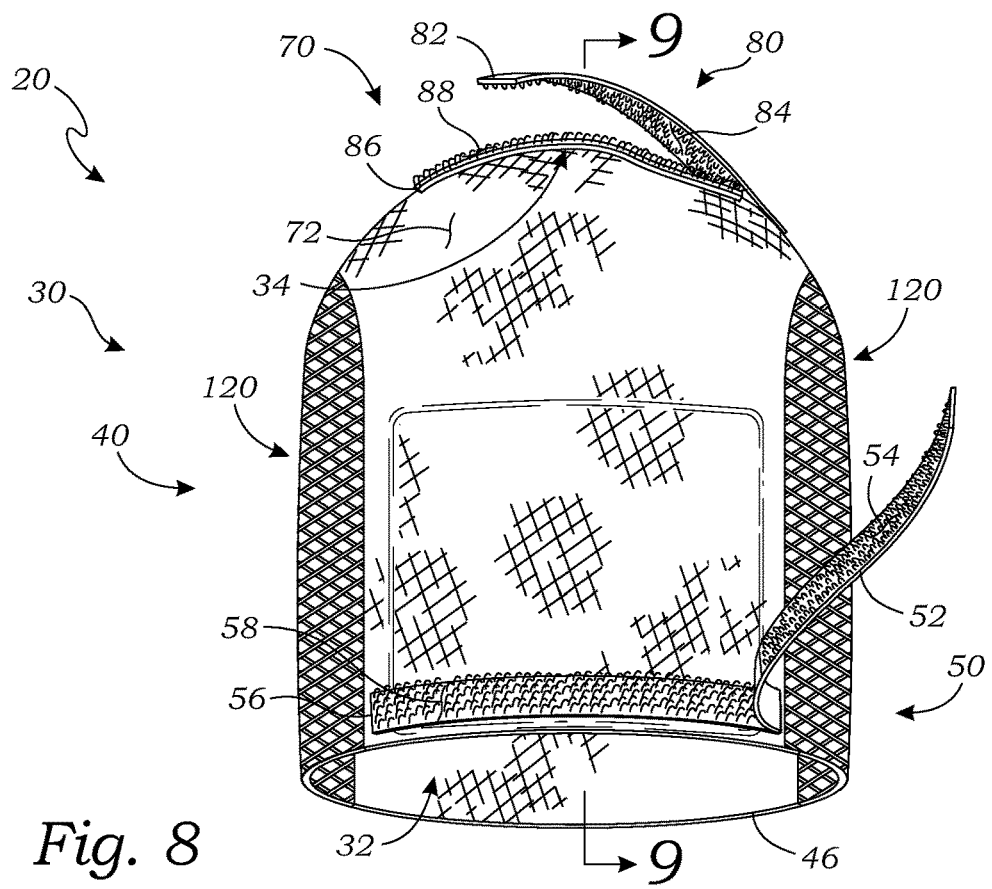
FIG. 8 is a perspective view of a further alternative exemplary anesthesia circuit holder and patient protection device, in accordance with at least one embodiment.
Figure 9:
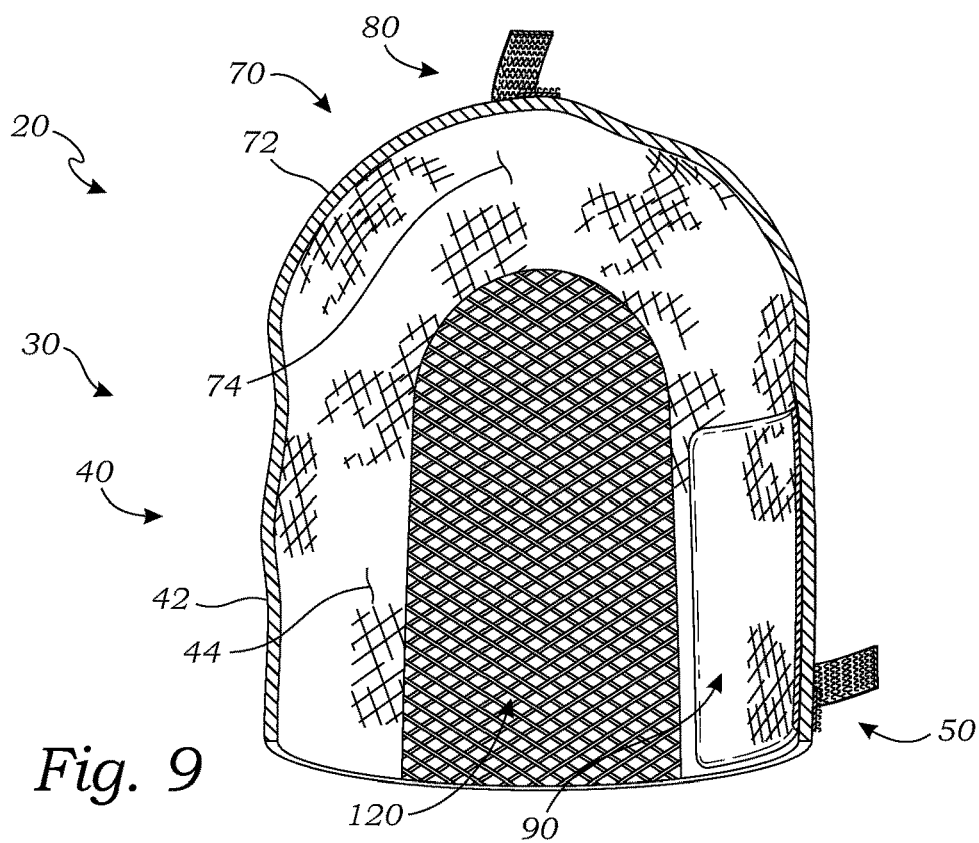
FIG. 9 is a side cross-sectional view thereof, in accordance with at least one embodiment.

Referring briefly to FIGS. 8 and 9, in yet another alternative exemplary embodiment of a combination anesthesia circuit holder and patient protection device 20 according to aspects of the present invention, here the hat-like body 30 is formed from a combination of panels stitched or otherwise joined together rather than from a single material or unitary construction. Specifically, side inserts 120 are formed on opposite sides of the perimeter portion 40 of the body 30 to provide breathability and comfort and potentially other properties such as elasticity. Such a hat-like body 30 may be formed from any suitable manufacturing process now known or later developed, with here the body 30 being generally comprised of a central portion of a first material that when laid flat would be substantially rectangular and when curved or bent may be of sufficient size and shape to define the front, top, and back regions of the hat-like body 30, leaving somewhat arched openings on opposite sides that are then filled in by the opposite side inserts 120, which inserts 120 it will be appreciated complete the body 30 in its hat-like configuration. Once more, the side inserts 120 may be stitched or otherwise attached to the edges of the central portion when it is curved or formed into the hat shape. Both the central region defining the top portion 70 and part of the perimeter portion 40 and the side inserts 120 may be formed of any suitable material now known or later developed having the desired comfort, elasticity/stretchability, and/or breathability, including but not limited to cotton, polyester, nylon, spandex/elastane, or any blends thereof. The side inserts 120 may be a different material from the rest of the body 30 in every respect, or may be the same material but just thinner or a more open weave in order to provide the reduced weight and increased breathability. Again, a variety of configurations and materials are possible according to aspects of the present invention without departing from its spirit and scope. With further reference to particularly the side cross-sectional view of FIG. 9, here in the alternative exemplary embodiment the padded region 90 is formed integrally with the perimeter portion 40 of the body 30, whether affixed to the inner surface 44 thereof or formed integrally with or within the body 30, thus not requiring a pocket 60 (FIG. 2) for receipt of a removable pad 90 as in the prior exemplary embodiment of FIGS. 1-4.

Figure 10:
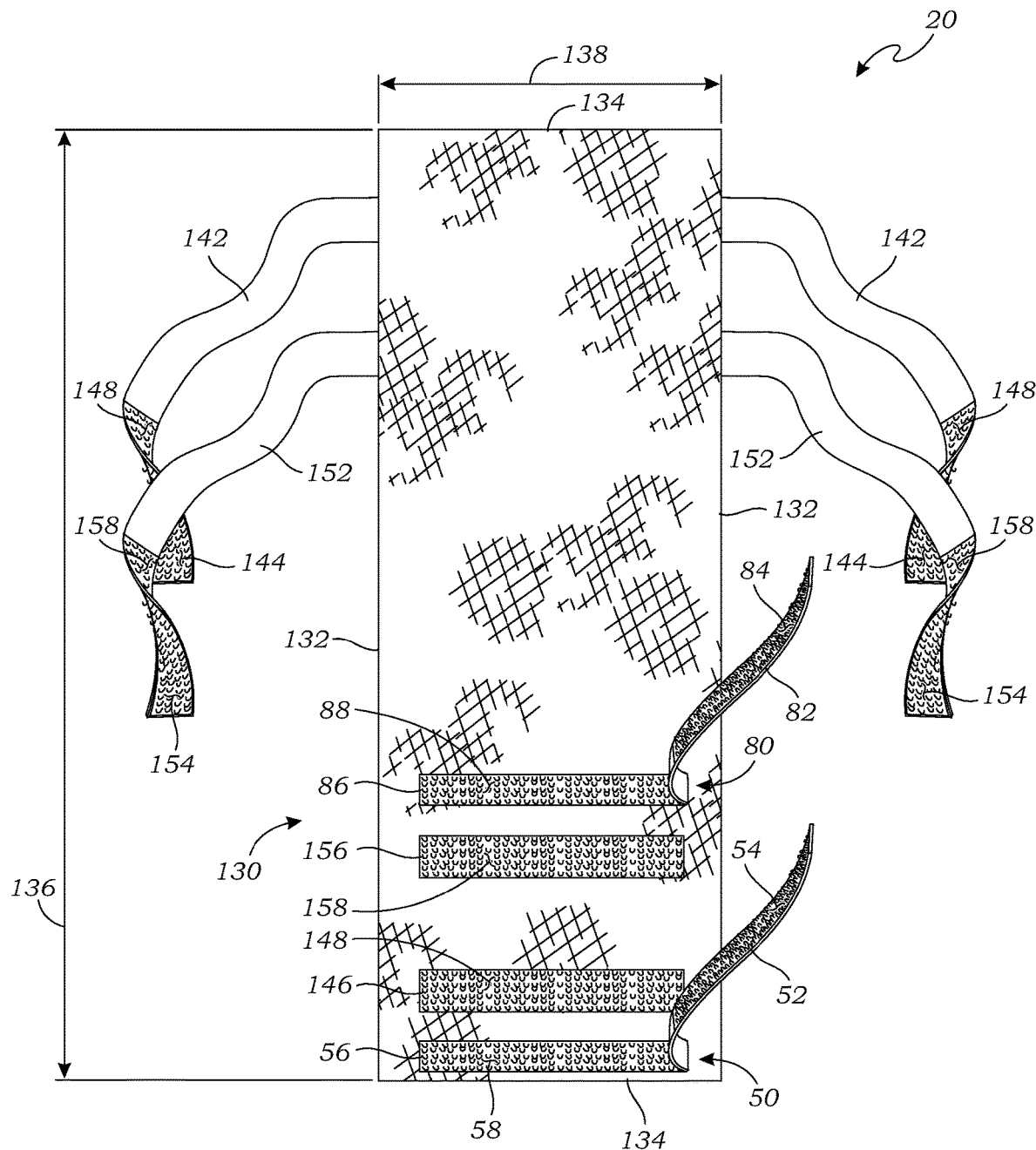
FIG. 10 is a front view of a still further alternative exemplary anesthesia circuit holder and patient protection device, in accordance with at least one embodiment.
Figure 11:
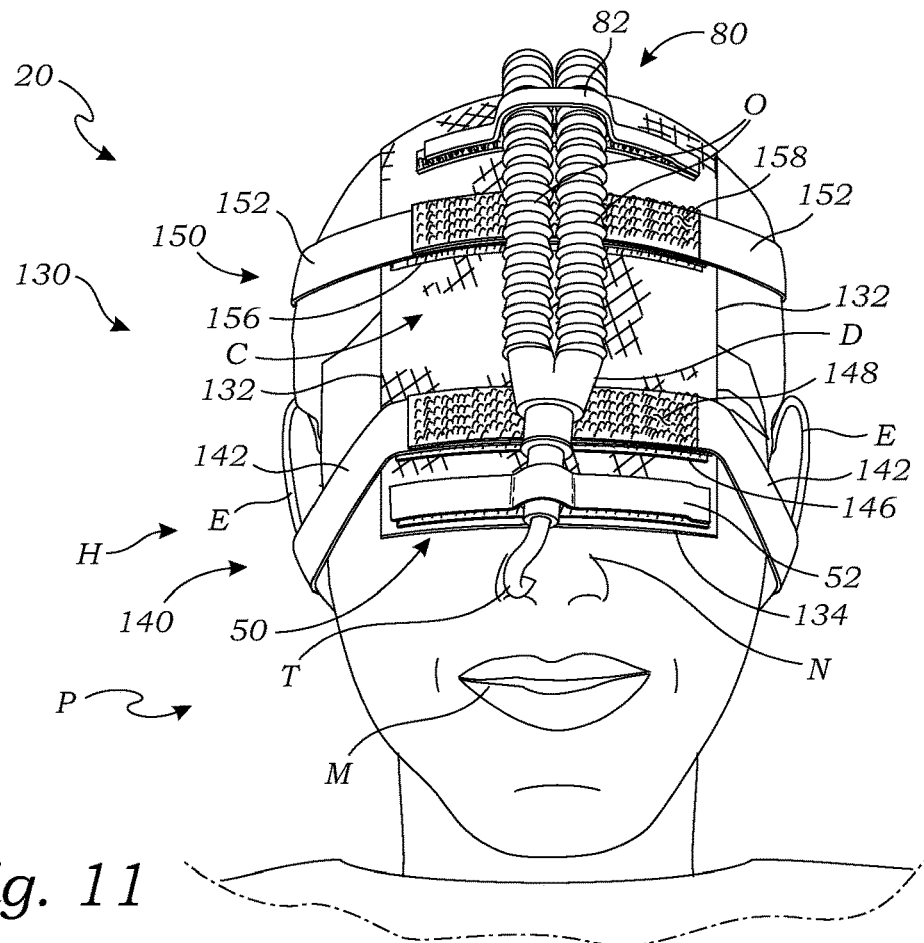
FIG. 11 is a reduced scale front perspective view thereof in use, in accordance with at least one embodiment.
Figure 12:
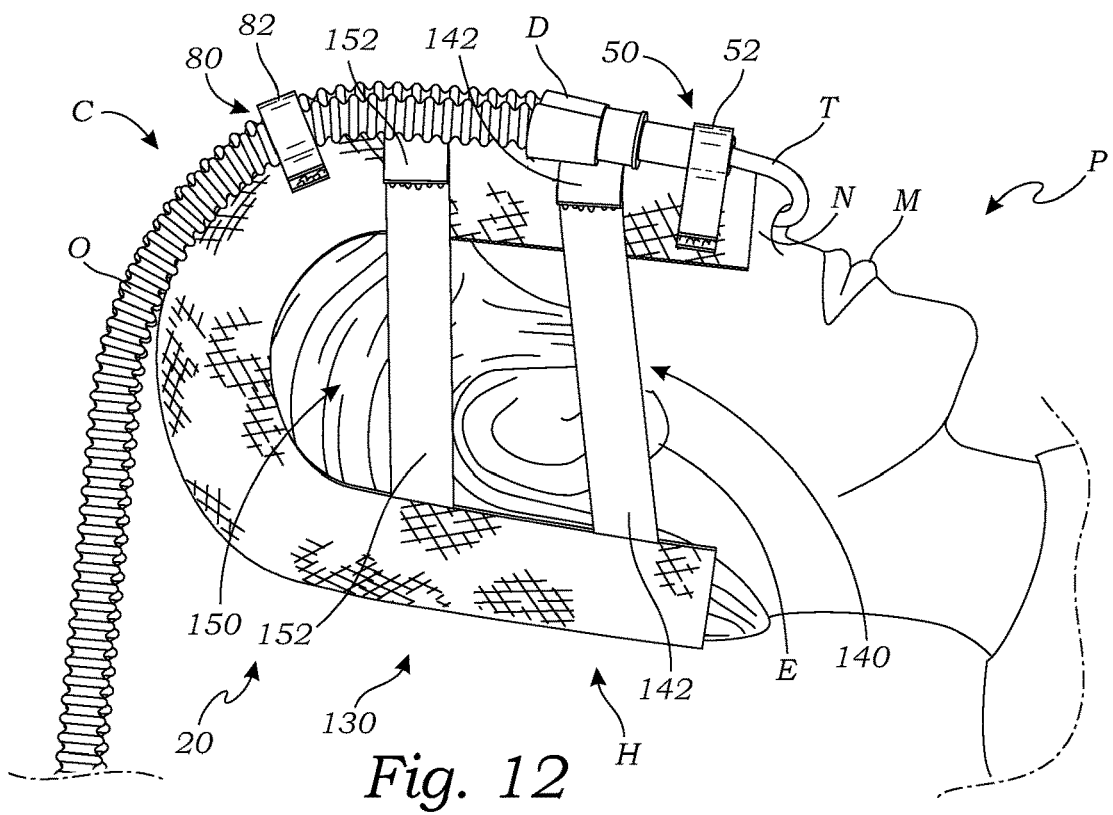
FIG. 12 is a side perspective view thereof in use, in accordance with at least one embodiment.

Turning to FIGS. 10-12, there is shown yet another alternative exemplary embodiment of a combination anesthesia circuit holder and patient protection device 20 according to aspects of the present invention. Here, the device 20 is configured as a substantially flat and rectangular body 130 having a pair of strap assemblies 140, 150 for selectively securing the body 130 about the head H of a patient P. At what is effectively the front end or portion of the body 130 when in use as shown in FIGS. 11 and 12 there are again formed an outwardly-facing front strap assembly 50 for selectively securing a nasal endotracheal tube T, connector D, or other such component of a breathing circuit C and a top strap assembly 80 for securing the circuit C or circuit hose(s) O particularly, similar to the arrangement in other exemplary devices 20 shown and described herein. Further, adjacent to the front and top strap assemblies 50, 80 there are also formed or affixed second strap portions 146, 156 associated with the respective strap assemblies 140, 150 configured for securing the device 20, and the body 130 specifically, about the head H. As shown, there are provided a first or lower strap assembly 140 comprising one or more strap portions 142 and an offset second or upper strap assembly 150 comprising one or more strap portions 152, each such strap portions 142, 152 attached or formed at the end of the body 130 opposite the front and top strap assemblies 50, 80 and the second strap portions 146, 156 so as to extend laterally therefrom, or as in the exemplary embodiment shown to extend somewhat perpendicularly from the lengthwise edges 132 of the body 130. More specifically, the first strap portions 142, 152 associated with the respective lower and upper strap assemblies 140, 150 may be a single piece of material affixed to or formed on or with the body 130 at an intermediate location so as to form the oppositely-extending strap portions 142, 152 at the opposite ends thereof. Or, each strap portion 142, 152 may be separately formed on or affixed to the body 130 so as to extend therefrom as desired. Those skilled in the art will appreciate that any manner of fabrication or assembly of such a body with straps, whether now known or later developed, is possible according to aspects of the present invention. In one exemplary embodiment, each first strap portion 142, 152 and the associated second strap portion 146, 156 are sewn or stitched on the body 130. It will also be appreciated that while in the illustrated embodiment the lower and upper strap assemblies 140, 150, or the second strap portions 146, 156 specifically, are shown as being intermediate the front and top strap assemblies 50, 80, such is not required, as will be further appreciated with reference to the alternative exemplary embodiment of FIGS. 13-15; rather, the various strap assemblies 50, 80, 140, 150 may be arranged in any desired manner to suit a particular application, both in terms of sequence and proximity as well number—that is, while two circuit securement strap assemblies 50, 80 and two device securement strap assemblies 140, 150 are shown, those skilled in the art will appreciate that the invention is not so limited but that a variety of other such configurations are possible according to aspects of the present invention. With continued reference to FIG. 10, it can be seen that each first strap portion 142, 152 is formed with a respective first fastener portion 144, 154 configured to selectively engage an outwardly-facing second fastener portion 148, 158 of the respective second strap portion 146, 156, more about which is said below in connection with FIGS. 11 and 12 and the device 20 in use. As with the front and top strap assemblies 50, 80, the lower and upper strap assemblies 140, 150 may be formed having any suitable removably engageable materials, fasteners, or the like now known or later developed, including but not limited to hook-and-loop fasteners, adhesives, snaps, buttons, zippers, buckles, and clips. In the illustrated embodiment, the strap assemblies 140, 150 each comprise hook-and-look fastener strap portions 144, 148, 154, 158, with it again not mattering which fastener portion contains the "hooks" and which the "loops." The body 130 may again be formed, in whole or in part, of any suitable material now known or later developed having the desired comfort, elasticity/stretchability, breathability, and/or padding or protection, including but not limited to cotton, polyester, nylon, spandex/elastane, other woven or knitted fabrics or textiles, foams, rubbers, or any blends thereof, and in any thicknesses, densities, or other properties to suit a particular application according to aspects of the present invention.

With reference particularly to FIGS. 11 and 12, in use, the combination anesthesia circuit holder and patient protection device 20 configured as a somewhat rectangular body 130 would be applied to or worn by the patient P as by positioning the front portion of the body 130 having the front and top strap assemblies 50, 80 over the patient's head H and face with particularly the lower or adjacent widthwise edge 134 lying across the nose N such that the eyes (not shown) of the patient P are covered. The remainder of the body 130 would then be pulled or curved over the top of the head H and around the back of the head H until the opposite widthwise edge 134 is positioned adjacent the base of the skull or the upper region of the neck as shown, with the first strap portions 142, 152 laying loose to both sides of the patient's head H. Those skilled in the art will appreciate that alternatively, and in practice, the patient P may first lay their head H on the back portion of the device body 130, again with the straps 142, 152 laid out to either side, and the body 130 then pulled up and over the top of the head H until the front region is laid over the face as shown and described. Either way, with the device body 130 so arranged or positioned, the device 20 is secured about the patient's head H by simply pulling the first strap portions 142, 152 up and about the head H and temporarily affixing or attaching to the lower and upper first fastener portions 144, 154 to the respective lower and upper second fastener portions 148, 158 of the respective lower and upper second strap portions 146, 156. In one embodiment, the lower and upper first strap portions 142, 152 "meet in the middle" with each attaching to the same lower and upper second strap portions 146, 156, or to a common second fastener portion 148, 158. In another embodiment, as shown, the lower and upper first strap portions 142, 152 overlap—accordingly, a further lower and upper second fastener portion 148, 158 is shown as being formed or affixed on the free ends of the respective lower and upper first strap portions 142, 152 opposite the respective lower and upper first fastener portion 144, 154, whereby when either of the first strap portions 142, 152 is wrapped around and affixed to the respective second strap portion 146, 156, as by removably engaging the first fastener portion 144, 154 of a single first strap portion 142, 152 with the second fastener portion 148, 158 formed on the respective second strap portion 146, 156, it will be appreciated that at the same time the further second fastener portions 148, 158 formed on the back sides of the respective strap portions 142, 152 are accessible to then removably engage with the respective first fastener portions 144, 154 of the other respective first strap portions 142, 152. Those skilled in the art will appreciate that the lower and upper strap assemblies 140, 150, and the respective lower and upper strap portions 142, 152 specifically, may be formed of any suitable material now known or later developed having the desired comfort, elasticity/stretchability, breathability, and/or padding or protection, including but not limited to cotton, polyester, nylon, spandex/elastane, other woven or knitted fabrics or textiles, foams, rubbers, or any blends thereof, and in any thicknesses, densities, or other properties to suit a particular application according to aspects of the present invention. It is noted that throughout, the first strap assembly 140 is referred to as the "lower" strap assembly based on the position of such strap assembly 140 in use as shown in FIGS. 11 and 12, and thus the position of the second strap portions 146, 156 particularly, rather than the position of the first strap portions 142, 152 when the device 20 is laid flat as illustrated in FIG. 10. Further regarding use of the alternative exemplary device 20 as shown and described in connection with FIGS. 10-12, it can be seen that the locations of the lower and upper strap assemblies 140, 150, and the first and second strap portions 142, 146, 152, 156 particularly, are such that when worn the lower strap assembly 140 is somewhat over the patient's eyes (not shown) with the lower first straps 142 passing along the patient's upper cheek area and across or beneath the ears E in the vicinity of the ear lobes so as to connect to or apply tension from the area at the base of the skull, which it will appreciate serves to comfortably retain the device 20 in place and discourage its movement toward the top of the head H or any such tendency to "slip off" during use; the upper strap assembly 150 is somewhat over the patient's forehead and so the upper first strap portions 152 wrap around the sides of the head H above the ears E. It will be further appreciated that the flexibility and/or elasticity of the lower and upper first strap portions 142, 152 allows for shifting or repositioning of the straps 142, 152 as desired by the clinician during placement and use of the device 20. Advantageously, the device may be so secured on the patient's head H first before then securing the circuit C, which again entails essentially fastening the tube T within the front strap assembly 50 and the circuit hoses O within the top strap assembly 80 as herein described. It will be further appreciated that one or both of the lower and upper strap assemblies 140, 150 may also be secured over the circuit C for its further retention as desired and that, in any event, the presence of the lower and upper strap assemblies 140, 150, and particularly the upwardly-facing second fastener portions 148, 158 formed on the backs of the respective lower and upper first strap portions 142, 152 would provide further frictional resistance to axial or sliding movement of the circuit C during use. As best seen in FIG. 12, a somewhat arched side region is formed within the space bounded by the lengthwise edge 132 of the body 130 as the device 20 is worn on the head H, which region is effectively closed in with a breathable mesh or other such material in the alternative exemplary embodiment of FIGS. 8 and 9 so as to form the device 20 in a hat-like configuration, which arched region here remains open, except for where the straps 142, 152 cross, again for breathability and comfort of the patient P while still covering and protecting the critical areas of the face and other areas of the head across which the circuit C may lie or that may be more like to bear the weight or impact of a person or object during any particular surgical procedure, it being appreciated that effectively the narrower the body 130 the wider the side openings when the device 20 is in use. Once again, a variety of such combination anesthesia circuit holder and patient protection device 20 configurations are possible according to aspects of the present invention without departing from its spirit and scope.

Further regarding the alternative exemplary device 20 of FIGS. 10-12, dimensionally, noting again with reference to Table 2 above that in adults the average biocular breadth, or the distance from the outer corners of the eyes, is in the range of four to five inches (4-5 in.) and the average bitragion breadth from the right tragion to the left (or essentially between the outer ear notches) is in the range of five to six inches (5-6 in.), it is preferable that the width 138 of the body 130, or the distance between opposite lengthwise or side edges 132, is in the range of at least four to six inches (4-6 in.). As for the overall length 136 of the body 130, it is first noted again with reference to Table 1 above that for adults the average vertical distance from the nasal root depression between the eyes (sellion) to the top of the head is in the range of four to four-and-a-half inches (4-4.5 in.) and the average vertical distance from the midpoint of the lips (stomion) to the top of the head is in the range of seven to seven-and-a-half inches (7-7.5 in.), and so taking the midpoint therebetween to be an intermediate location along the nose below the bridge of the nose and the eyes, it follows that a vertical distance from such location to the top of the head is in the range of five-and-a-half to six inches (5.5-6 in.) in the average adult. Similarly, for the back of the head, the distance from the top of the head down to the mouth substantially corresponds to the distance from the top of the head down to the base of the skull or the location around the sides and back of the head at and below the ears, or is again approximately seven to seven-and-a-half inches (7-7.5 in.) in the average adult. Finally, it is again noted as above that the average adult head circumference is in the range of twenty to twenty-five inches (20-25 in.) while for children it is in the range of eighteen to twenty-two inches (18-22 in.), which translates to diameters nominally ranging from approximately six to eight inches (6-8 in.) for adult head or hat sizes and from approximately five-and-a-half to seven inches (5.5-7 in.) for children. Accordingly, and allowing for the patient's hair, it follows that the overall length 136 of the body 130, or the distance from one widthwise edge 134 to the other, if one edge 134 is to be across the patient's nose N and the device 20 is to go around the top and back of the head H to the base of the skull, would be on the order of eighteen to twenty-four inches (18-24 in.), though again it will be appreciated that other sizes outside this range may be employed to suit particular clinical applications according to aspects of the present invention without departing from its spirit and scope. The thickness of the body 130 may be in the range of one-quarter inch (¼ in.) to an inch (1 in.) or more, which thickness may be constant along the length of the body 130 or may vary, such as particularly in the front region beneath the front and top strap assemblies 50, 80 where a thicker padded area for protection of the patient's nose and eyes may be desirable. As for the lower and upper strap assemblies 140, 150, and the lower and upper first strap portions 142, 152 particularly, the length of such straps 142, 152 measured from the lengthwise edge 132 in the vicinity of where the straps 142, 152 originate would be on the order of nine to thirteen inches (9-13 in.), or approximately half the average circumference of the head or approximately double the width of the body 130. Once more, those skilled in the art will appreciate that a variety of other lengths and configurations of the straps 142, 152 are possible according to aspects of the present invention depending on a number of factors, including but not limited to the means of securing the straps 142, 152 at the front of the device 130 and the material and thus elasticity of the straps 142, 152 themselves. It will be further appreciated with continued reference to FIGS. 11 and 12 that the width of the lower and upper strap portions 142, 152 may be in the range of a half inch to three inches (0.5-3 in.), though is typically on the order of one inch (1 in.) wide.

Figure 13:
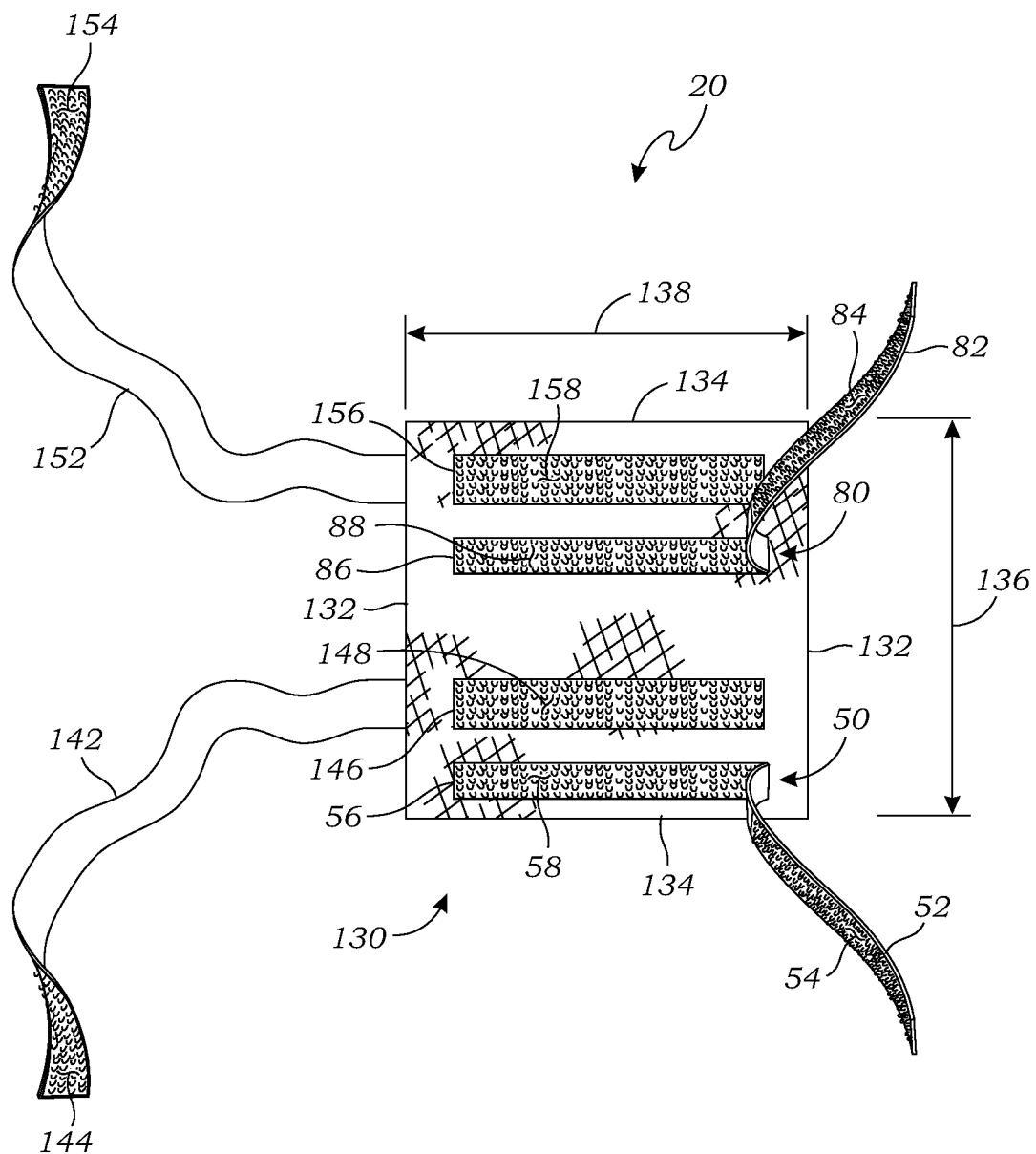
FIG. 13 is a front view of a still further alternative exemplary anesthesia circuit holder and patient protection device, in accordance with at least one embodiment.
Figures 14, 15:
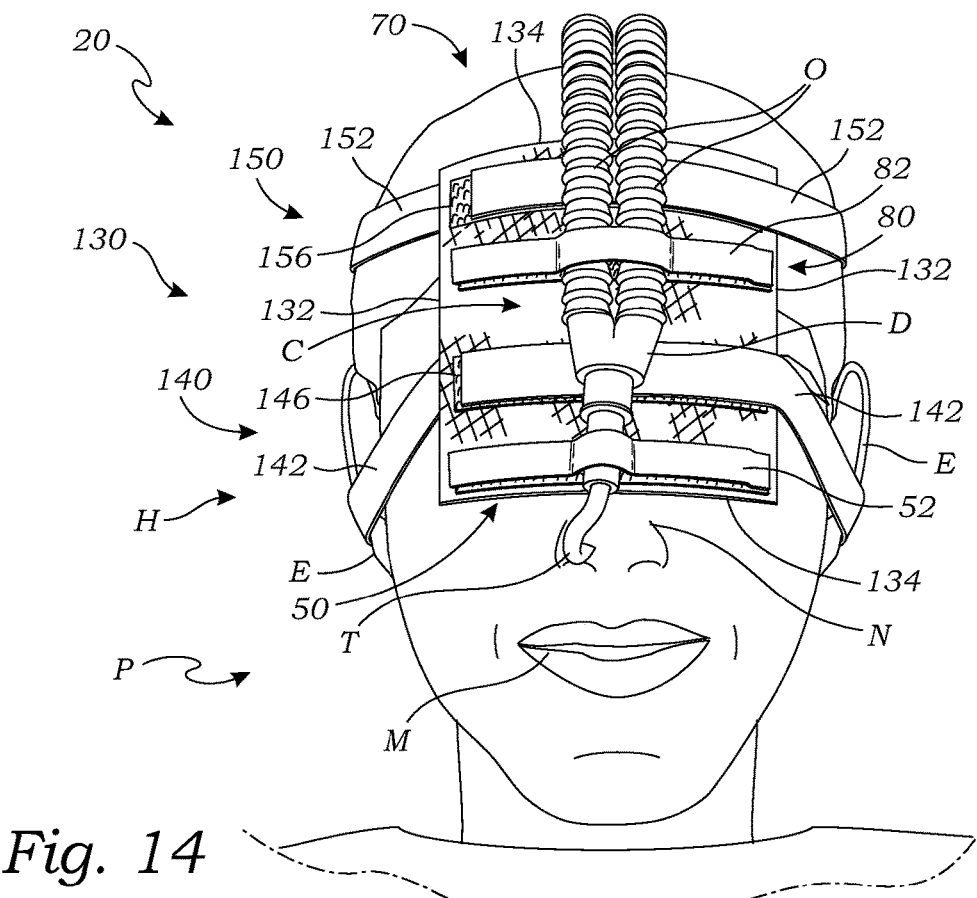
FIG. 14 is a reduced scale front perspective view thereof in use, in accordance with at least one embodiment.
FIG. 15 is a side perspective view thereof in use, in accordance with at least one embodiment.

Referring next to FIGS. 13-15, there is shown yet another alternative exemplary embodiment of a combination anesthesia circuit holder and patient protection device 20 according to aspects of the present invention, here configured much like that of FIGS. 10-12 except the body 130 being much smaller so as to cover a portion of the front of the head H or face but not the top or back of the head H, with the strap assemblies 140, 150 modified accordingly. That is, the body 13 is a relatively smaller rectangle or substantially square in this alternative embodiment—recalling that the distance from the outer corners of the eyes, is in the range of four to five inches (4-5 in.) and the average bitragion breadth from the right tragion to the left (or essentially between the outer ear notches) is in the range of five to six inches (5-6 in.), it is preferable that the width 138 of the body 130, or the distance between opposite lengthwise side edges 132, is preferably in the range of at least four to six inches (4-6 in.). Further noting once more that the distance from an intermediate location along the nose N to the top of the head or a location above the eyes and forehead is in the range of five-and-a-half to six inches (5.5-6 in.) in the average adult, it is desirable that the length 136 of the body, or the distance between opposite widthwise edges 134 is at least on the order of six inches (6 in.) or more. Thus, by way of illustration and not limitation, the body 130 of the alternative device 20 of FIGS. 13-15 may be a six inch by six inch (6 in.×6 in.) square, though again it will be appreciated that a variety of other square and non-square shapes and sizes are possible according to aspects of the present invention. Moreover, as between the embodiments of FIGS. 10-12 and that of FIGS. 13-15, it will be appreciated that a virtually infinite range of other intermediate configurations are possible, just as between such flat pad-like devices 20 of FIGS. 10-15 and the hat-like devices 20 of FIGS. 1-9. That is, as an intermediate configuration between the embodiments of FIGS. 10-12 and 13-15, a device 20 may be configured that is relatively wider at the front and back of the head H but narrower across the top of the head H (a somewhat hourglass profile) or that is wider only at the front of the head H, either way, such top region of the device 20 being sufficiently wide to accommodate circuit or sampling line securement, for example. In any case, when there is little to no structure provided by the device 20 at the back of the head H, it will be appreciated that, as shown best in FIG. 13, single lower and upper strap assemblies 140, 150 or more particularly single lower and upper first strap portions 142, 152 may be formed so as to extend from one lengthwise side or edge 132 of the body 130 so as to in use wrap around the back of the head and be removably affixed to the body 130 so as to thereby secure the device 20 on the head H. In a bit more detail, here, the lower and upper first strap portions 142, 152 are again formed having respective lower and upper first fastener portions 144, 154 configured to removably engage with respective lower and upper second fastener portions 148, 158 formed on the respective lower and upper second strap portions 146, 156 that are themselves affixed on or otherwise attached to or formed with the body 130. As such, in use, the straps 142, 152 may simply be wrapped around the head H and attached, thereby securing the device 20 on the head H. More particularly, as shown in FIGS. 14 and 15, the lower first strap 142 passes from the device body 130 over the check and across or beneath the ear E and around the back of the head H and up the other side before being attached to the lower second strap portion 146. Similarly, the upper first strap 152 passes from the device body 130 along the side of the head H above the ear E and again around the back of the head H and up the other side before being attached to the upper second strap portion 156. Again, such strap assemblies 140, 150 may be of any material, configuration, number, and engagement or attachment means now known or later developed, such that the illustrated two such strap assemblies 140, 150 are to be understood as merely exemplary and non-limiting. Once more, the body 130 is also formed with front and top strap assemblies 50, 80 for selectively securing an anesthesia circuit C as herein described, which strap assemblies 50, 80, 140, 150 may be in any arrangement in terms of sequence and proximity, the arrangement illustrated being merely exemplary. As best seen in FIG. 15, the device 20 and particularly the body 130 here substantially covers the upper portion of the face of the patient P from the nose to the forehead and, from side to side, both eyes (not shown), while the remainder of the patient's head H is uncovered, other than the straps 142, 152 for further breathability and comfort, as may particularly be appropriate for less time-consuming or invasive procedures. In any such flat or pad-like device 20 wherein lower and/or upper first strap portions wrap around the sides of the patient's head H, it will be appreciated that a side strap assembly 110 (FIGS. 5-7) may still be provided for low-profile retention of a circuit C having an elbow L as by positioning one or more such side strap assembly 110 on one or more of the lower and upper strap assemblies 140, 150, and the lower and upper first strap portions 142, 152, specifically, in any appropriate manner now known or later developed. Once again, any such arrangements of a combination anesthesia circuit holder and patient protection device 20 are possible according to aspects of the present invention, including but not limited to the size, shape, and construction of the body 130 and the locations and configurations of any related strap assemblies 50, 80, 140, 150, without departing from the spirit and scope of the invention.

EXAMPLES

The following non-limiting examples are provided for illustrative purposes only in order to facilitate a more complete understanding of representative embodiments now contemplated. These examples are intended to be a mere subset of all possible contexts in which the combination anesthesia circuit holder and patient protection device 20 may be utilized. Thus, these examples should not be construed to limit any of the embodiments described in the present specification, including those pertaining to particular device configurations and/or methods and uses thereof. Ultimately, the combination anesthesia circuit holder and patient protection device 20 may be utilized in virtually any context where safely, comfortably, and effectively holding an anesthesia circuit or the like while also protecting the patient during oral, facial or other such surgery with minimal interference with the surgical site is desired.

Example 1

Surgical Installation of Dental Implant

This example demonstrates use of an exemplary combination anesthesia circuit holder and patient protection device in the context of surgical installation of a dental implant.

A woman in her mid-50's presented with a long-span edentulous space in the lower left posterior quadrant. After an intra-oral exam, treatment options were discussed and the patient elected a dental implant approach over conventional treatment with a removable partial denture, and in-office surgery was scheduled. On the day of the surgery the patient underwent general anesthesia under the care of a licensed anesthesiologist, wherein a mixture of anesthetic gas and oxygen was administered through a nasal breathing apparatus in the form of a nasal endotracheal tube and anesthesia circuit. After the patient was unconscious a nasal tracheal tube was inserted through the nose. To secure the circuit and protect the patient's head and eyes during the procedure, a combination anesthesia circuit holder and patient protection device in the form of a hat was pulled over the head and eyes of the patient down to the end of the nose. With the tube in position and administration of the anesthetic underway and the patient comfortable and unconscious, the circuit was secured on the hat-like device using a pair of Velcro® straps, one at the front of the hat just across the eyes and one at top of the hat and head, thus maintaining the circuit securely and with a low profile over the top of the patient's head away from the mouth, where the dental surgeon had full and unobstructed access. Accordingly, surgery proceeded following protocol for posterior edentulousness, including site preparation and then placement of three 3.75 mm diameter spline titanium plasma spray (TPS)-coated screw implants—in the second premolar, first molar, and second molar areas with a cantilevered first premolar. A pad within the hat-like device was situated over the patient's nose and eyes for further protection during the procedure and as a further buffer between the patient and the anesthesia circuit, particularly in the face and forehead region, again including the eyes and bridge of the nose. Accordingly, the patient experienced no discomfort during the procedure and complained of no adverse effects of the anesthesia circuit post-surgery other than slight nasal passage sensitivity, and certainly no impact whatsoever to the patient's eyes. In a follow-up procedure again following a similar anesthetic regimen, the implants were exposed with a mid-crestal incision and spline temporary gingival healing cuffs were placed and the soft tissues were then allowed to heal around the cuffs. Subsequently, the finished substructure was seated on the implant abutments and secondary tooth castings were cemented. Fundamentally, all such procedures as required for complete dental reconstruction that necessitated anesthesia were carried out employing the hat-like head covering device for patient protection and anesthesia circuit retention in a convenient and effective manner.

Example 2

Oral-Facial Reconstructive Surgery

This example demonstrates use of an exemplary combination anesthesia circuit holder and patient protection device in the context of oral-facial reconstructive surgery.

A 44-year-old male presented with a mass in the lower mandible requiring removal of a portion thereof and related reconstruction. Specifically, clinical and radiographic findings were of a radiolucent lesion of the lower right mandibular ramus measuring 26 mm×19 mm. The surgical procedure required general anesthesia via administration of an intravenous anesthetic under the care of an anesthesiologist. As the anesthesia was administered the patient was intubated using a nasal endotracheal tube for purposes of airway maintenance and patient ventilation (oxygen delivery). To secure the anesthesia circuit and protect the patient's head and eyes during the procedure, a combination breathing circuit holder and patient protection device in the form of a hat was pulled over the head and eyes of the patient, leaving the nose exposed for insertion of the nasal endotracheal tube. Once the tube was in position and continued anesthesia administration and monitoring of the patient's vitals was underway, the breathing circuit was secured on the hat-like device using a pair of Velcro® straps, one at the front of the hat just across the eyes and one at top of the hat and head, shifting the circuit to the patient's left as the patient's head was also turned to the left, exposing the right side of the face as the principal surgical site. Thus, implementation of the hat-like circuit holder and patient protection device maintained the circuit securely and with a low profile over the left-of-center top of the patient's head, away from the right side of the face and jaw, whereby the oral-facial surgeon had full and unobstructed access to the surgical site. Accordingly, surgery proceeded according to plan and without incident relative to placement and maintenance of the nasal endotracheal tube and without any trauma to the patient beyond the surgery site, including the nearby ear and unaffected head regions, in part due to the hat-like head covering device, such that even placement on the head of the surgeon's hands and other instruments in manipulating the head and jaw during surgery posed no threat or caused no adverse consequence to the patient.

Example 3

Surgical Installation of Dental Implant

This example demonstrates use of a further exemplary combination anesthesia circuit holder and patient protection device in the context of surgical installation of a dental implant.

A 60-year-old man presented with a failed post-and-core crown on a central incisor (tooth #8) resulting from recurrent decay. After an intra-oral exam, treatment through extraction of the affected tooth and immediate replacement with a tapered implant and provisional crown was elected. On the day of the surgery the patient underwent general anesthesia under the care of a licensed anesthesiologist, wherein a mixture of anesthetic gas and oxygen was administered through a nasal breathing apparatus in the form of a nasal endotracheal tube and anesthesia circuit. After the patient was unconscious a nasal tracheal tube was inserted through the nose. To secure the circuit and protect the patient's head and eyes during the procedure, a combination anesthesia circuit holder and patient protection device in the form of a pad with straps was placed over the head and eyes of the patient down to the end of the nose as by attaching straps around the back of the head to the front. With the tube in position and administration of the anesthetic underway and the patient comfortable and unconscious, the circuit was secured on the pad-type device using a pair of Velcro® straps, one at the lower end of the pad in the vicinity of the eyes and one at top of the pad and head, thus maintaining the circuit securely and with a low profile over the top of the patient's head away from the mouth, where the dental surgeon had full and unobstructed access. Accordingly, surgery proceeded following protocol via atraumatic extraction of the affected incisor tooth, creation and placement of the implant osteotomy, seating and trimming a temporary abutment, suturing the surgical site, and fabricating and affixing a screw-retained provisional crown. The pad-type combination anesthesia circuit holder and patient protection device being situated over the patient's nose and eyes for protection during the procedure and as a buffer between the patient and the anesthesia circuit, particularly in the face and forehead region, again including the eyes and bridge of the nose, the patient complained of no adverse effects of the anesthesia circuit post-surgery other than slight nasal passage sensitivity, and certainly no impact whatsoever to the patient's eyes. In a follow-up procedure three months later, a transfer post was attached to the implant so the final impression could be taken, a custom abutment and anterior crown were fabricated, the new abutment was tightened into place, and the final crown was cemented over the custom abutment. Fundamentally, all such procedures as required for complete dental reconstruction that necessitated anesthesia were carried out employing the pad-type device for patient protection and anesthesia circuit retention in a convenient and effective manner.

Aspects of the present specification may also be described as follows:

1. A combination anesthesia circuit holder and patient protection device apparatus configured to be worn on the head of a patient so as to cover at least the eyes and to temporarily secure an anesthesia circuit, the apparatus comprising: a body having at least a perimeter portion and a pad configured at the perimeter portion for being positioned over the eyes of the patient; and at least two strap assemblies formed on the body, a front strap assembly positioned on a front outer surface of the body and a top strap assembly offset vertically from the front strap assembly and positioned on a top outer surface of the body, the strap assemblies cooperating to temporarily secure the anesthesia circuit; whereby placement of the apparatus on the head of the patient provides protection of at least the eyes while safely and effectively securing the anesthesia circuit in a relatively low-profile configuration with relatively minimal interference with a surgical site.

2. The apparatus of embodiment 1 wherein the body is hat-like, further having a top portion and wherein the perimeter portion is substantially continuous circumferentially and integral with the top portion, a perimeter outer surface of the perimeter portion defining the front outer surface, and the top outer surface being formed on the top portion.

3. The apparatus of embodiment 1 or embodiment 2 wherein the pad is integral with the perimeter portion.

4. The apparatus of embodiment 1 or embodiment 2 wherein the pad is removably engaged with the perimeter portion.

5. The apparatus of embodiment 4 further comprising a pocket formed on a perimeter inner surface of the perimeter portion and configured for removable receipt of the pad.

6. The apparatus of embodiment 5 wherein the pocket is formed by a panel affixed to the perimeter inner surface along opposite substantially vertical side seams and further along a bottom seam offset from a lower perimeter edge of the perimeter portion so as to define a pocket opening toward the top portion for removable receipt of the pad.

7. The apparatus of embodiment 6 wherein the pad is formed having opposite side edges corresponding to the side seams, a bottom edge corresponding to the bottom seam, and a top edge corresponding to the opening.

8. The apparatus of embodiment 7 wherein the distance between opposite side edges is in the range of four to six inches (4-6 in.).

9. The apparatus of embodiment 7 wherein the distance between opposite side edges is at least four inches (4 in.).

10. The apparatus of any of embodiments 7-9 wherein the distance between the bottom and top edges is in the range of five to six inches (5-6 in.).

11. The apparatus of any of embodiments 7-9 wherein the distance between the bottom and top edges is at least five inches (5 in.).

12. The apparatus of any of embodiments 1-11 wherein the front strap assembly comprises a front first strap portion affixed at one end to the perimeter outer surface and a front second strap portion affixed along its length substantially parallel to and offset from a lower perimeter edge of the perimeter portion and adjacent to and substantially aligned with the front first strap portion, whereby the front first strap portion is selectively and temporarily engageable with the front second strap portion, the front strap assembly being configured to selectively secure one of a tube or a connector of the anesthesia circuit between the front first and second strap portions and thus the overall anesthesia circuit.

13. The apparatus of embodiment 12 wherein the top strap assembly comprises a top first strap portion affixed at one end to the top outer surface and a top second strap portion affixed along its length substantially parallel to and offset from the front second strap portion and adjacent to and substantially aligned with the top first strap portion, whereby the top first strap portion is selectively and temporarily engageable with the top second strap portion, the top strap assembly being configured to selectively secure one of a connector or a hose of the anesthesia circuit between the top first and second strap portions and thus the overall anesthesia circuit.

14. The apparatus of any of embodiments 1-13 wherein a lower perimeter edge of the perimeter portion defines an opening in the body opposite the top portion, and the top portion defines an apex of the body, whereby the distance across the opening defines a nominal width of the body and the distance from the opening to the apex defines a nominal height of the body.

15. The apparatus of embodiment 14 wherein the height is at least seventy-five percent (75%) of the width.

16. The apparatus of embodiment 14 wherein the height is greater than or equal to the width.

17. The apparatus of embodiment 14 wherein the width is in the range of six to eight inches (6-8 in.).

18. The apparatus of embodiment 14 wherein the width is at least six inches (6 in.).

19. The apparatus of embodiment 14 wherein the width is no greater than eight inches (8 in.).

20. The apparatus of any of embodiments 14-19 wherein the height is in the range of seven to nine inches (7-9 in.).

21. The apparatus of any of embodiments 14-19 wherein the height is at least seven inches (7 in.).

22. The apparatus of any of embodiments 14-19 wherein the height is no greater than nine inches (9 in.).

23. The apparatus of any of embodiments 1-22 further comprising at least one side strap assembly positioned on a side outer surface of the body, the side strap assembly oriented at an angle to the front strap assembly.

24. The apparatus of any of embodiments 1-23 further comprising first and second side strap assemblies positioned on opposite sides of the body.

25. The apparatus of embodiment 23 or embodiment 24 wherein the side outer surface is formed on the perimeter outer surface.

26. The apparatus of any of embodiments 23-25 wherein the side strap assembly comprises a side first strap portion affixed at one end to the side outer surface and a side second strap portion affixed along its length adjacent to and substantially aligned with the side first strap portion, whereby the side first strap portion is selectively and temporarily engageable with the side second strap portion, the side strap assembly being configured to selectively secure one of a connector or a hose of the anesthesia circuit between the side first and second strap portions and thus the overall anesthesia circuit when the anesthesia circuit includes an elbow.

27. The apparatus of embodiment 26 wherein the side strap assembly is substantially perpendicular to the front strap assembly and the elbow is a substantially ninety-degree (90°) elbow.

28. The apparatus of any of embodiments 1-27 wherein the body is of unitary construction.

29. The apparatus of any of embodiments 1-27 wherein the body is of modular construction.

30. The apparatus of any of embodiments 1-29 wherein the perimeter portion is of unitary construction.

31. The apparatus of any of embodiments 1-29 wherein the perimeter portion is of modular construction.

32. The apparatus of any of embodiments 1-31 wherein the perimeter portion comprises opposite side inserts.

33. The apparatus of embodiment 32 wherein the inserts are formed of a breathable material.

34. The apparatus of any of embodiments 1-33 wherein the body is substantially flat and defines a unitary perimeter portion and pad, a perimeter outer surface of the perimeter portion defining the front outer surface and the top outer surface.

35. The apparatus of any of embodiments 1-34 wherein the body is formed having opposite lengthwise edges and opposite widthwise edges, whereby the distance between the lengthwise edges defines a nominal width of the body and the distance between the widthwise edges defines a nominal length of the body.

36. The apparatus of embodiment 35 wherein the length is at least seventy-five percent (75%) of the width.

37. The apparatus of embodiment 35 wherein the length is greater than or equal to the width.

38. The apparatus of any of embodiments 35-37 wherein the width is in the range of four to six inches (4-6 in.).

39. The apparatus of any of embodiments 35-37 wherein the width is at least four inches (4 in.).

40. The apparatus of any of embodiments 35-37 wherein the width is no greater than six inches (6 in.).

41. The apparatus of any of embodiments 35-40 wherein the length is in the range of eighteen to twenty-four inches (18-24 in.).

42. The apparatus of any of embodiments 35-40 wherein the length is at least twenty-four inches (24 in.).

43. The apparatus of any of embodiments 35-40 wherein the length is no greater than eighteen inches (18 in.).

44. The apparatus of any of embodiments 35-40 wherein the length is in the range of five to six inches (5-6 in.).

45. The apparatus of any of embodiments 35-40 wherein the length is at least five inches (5 in.).

46. The apparatus of any of embodiments 1-45 further comprising a lower strap assembly formed on the body offset from the front and top strap assemblies and configured for selectively wrapping a portion of the head of the patient so as to secure the apparatus on the head.

47. The apparatus of embodiment 46 wherein the lower strap assembly comprises a lower first strap portion affixed at one end to the body so as to extend laterally from one or more lengthwise edge thereof and a lower second strap portion affixed along its length substantially parallel to and offset from the widthwise edges, whereby the lower first strap portion is selectively and temporarily engageable with the lower second strap portion, the lower strap assembly being configured to selectively secure at least a portion of the body of the apparatus on the head of the patient.

48. The apparatus of embodiment 46 or embodiment 47 further comprising an upper strap assembly formed on the body offset from the lower strap assembly and the front and top strap assemblies and configured for selectively wrapping a portion of the head of the patient so as to cooperate with the lower strap assembly in securing the apparatus on the head.

49. The apparatus of embodiment 48 wherein the upper strap assembly comprises an upper first strap portion affixed at one end to the body so as to extend laterally from one or more lengthwise edge thereof offset from the lower first strap portion and an upper second strap portion affixed along its length substantially parallel to and offset from the widthwise edges and the lower second strap portion, whereby the upper first strap portion is selectively and temporarily engageable with the upper second strap portion, the upper strap assembly being configured to selectively secure at least a portion of the body of the apparatus on the head of the patient.

50. The apparatus of any of embodiments 47-49 wherein the lower and upper first strap portions extend from both opposite lengthwise edges.

51. The apparatus of any of embodiments 47-50 wherein the lower and upper first strap portions are offset from the front and top strap assemblies.

52. The apparatus of any of embodiments 47-50 wherein the lower and upper first strap portions are adjacent to the front and top strap assemblies.

53. The apparatus of any of embodiments 47-52 wherein the lower and upper second strap portions are offset from the front and top strap assemblies.

54. The apparatus of any of embodiments 47-52 wherein the lower and upper second strap portions are adjacent to the front and top strap assemblies.

55. The apparatus of any of embodiments 1-54 wherein each strap assembly comprises a first strap portion affixed at one end to the body and a second strap portion affixed along its length to the body substantially aligned with the first strap portion, whereby the first strap portion is selectively and temporarily engageable with the second strap portion.

56. The apparatus of embodiment 55 wherein the first strap portion comprises a first fastener portion and the second strap portion comprises a second fastener portion, the first and second fastener portions configured for selective engagement in temporarily securing the first strap portion relative to the second strap portion.

57. The apparatus of embodiment 56 wherein the first and second fastener portions together define a hook-and-loop fastener.

58. A method of employing a combination anesthesia circuit holder and patient protection device apparatus as defined in any one of embodiments 1-57, the method comprising the steps of: placing the body of the apparatus over the eyes of the patient; and securing the anesthesia circuit within the front and top strap assemblies formed on the body.

59. The method of embodiment 58, further comprising the step of inserting the pad within the pocket formed within the body.

60. The method of embodiment 58 or embodiment 59, wherein the step of placing the body of the apparatus over the eyes of the patient comprises pulling the hat-like body down over the head and eyes.

61. The method of any of embodiment 58 or embodiment 59, wherein the step of placing the body of the apparatus over the eyes of the patient comprises positioning a top end of the body under the head and curving the bottom end of the body over the top of the head and at least a portion of the face and then strapping the body in place.

62. The method of embodiment 58 or embodiment 59, wherein the step of placing the body of the apparatus over the eyes of the patient comprises positioning the body directly over at least a portion of the face including the eyes and then strapping the body in place.

63. The method of any of embodiments 58-62, wherein the step of securing the anesthesia circuit within the front and top strap assemblies formed on the body comprises temporarily fastening one of the tube or the connector of the anesthesia circuit within the front strap assembly.

64. The method of any of embodiments 58-63, wherein the step of securing the anesthesia circuit within the front and top strap assemblies formed on the body further comprises selecting between the top strap assembly and a side strap assembly and temporarily fastening one of the connector or the hose of the anesthesia circuit therein.

65. A kit comprising a combination anesthesia circuit holder and patient protection device apparatus as defined in any one of embodiments 1-57.

66. The kit of embodiment 65, further comprising instructional material.

67. The kit of embodiment 66, wherein the instructional material provides instructions on how to perform the method as defined in any one of embodiments 58-64.

68. Use of a combination anesthesia circuit holder and patient protection device apparatus as defined in any one of embodiments 1-57 to provide relatively low profile anesthesia circuit retention so as to eliminate unnecessary obstruction of the surgical field while providing head and eye protection to the patient.

69. The use of embodiment 68, wherein the use comprises a method as defined in any one of embodiments 58-64.

In closing, regarding the exemplary embodiments of the present invention as shown and described herein, it will be appreciated that a combination anesthesia circuit holder and patient protection device is disclosed and configured for safely, comfortably, and effectively holding an anesthesia circuit or the like while also protecting the patient during oral, facial or other such surgery with minimal interference with the surgical site. Because the principles of the invention may be practiced in a number of configurations beyond those shown and described, it is to be understood that the invention is not in any way limited by the exemplary embodiments, but is generally directed to a device comprising a body formed as a hat sized and configured to be placed on a patient's head and pulled down over the eyes and having one or more strap assemblies situated on the front side and/or top portion of the body proximate a pad for further protection of the patient during use and is able to take numerous forms in providing such securement and protection functionality without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. The recitation of numerical ranges of values herein is merely intended to serve as a shorthand method of referring individually to each separate value falling within the range. Unless otherwise indicated herein, each individual value of a numerical range is incorporated into the specification as if it were individually recited herein. Similarly, all lists of values should be considered as inclusive of intermediate values unless the context indicates the contrary.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the application should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A combination anesthesia circuit holder and patient protection device apparatus configured to be worn on a head of a patient so as to cover at least the patient's eyes and further configured to temporarily secure an anesthesia circuit during an oral or facial surgical procedure, the anesthesia circuit comprising at least one connector and at least one hose, the apparatus comprising:
    a body formed as a hat having a circumferentially continuous perimeter portion defining an opening configured for receipt of the head of the patient and the body further having a top portion integral with the perimeter portion so as to form the hat, wherein the hat is configured to enclose and receive the head of the patient within the hat, the perimeter portion having a perimeter outer surface and the top portion having a top outer surface;
    a single pad positioned at the perimeter portion and integral with the body or inserted into a pocket of the body, the pad configured for being positioned over at least the eyes of the patient when the hat is positioned on the head of the patient, wherein the pad is located entirely within a front half of the body; and
    at least two strap assemblies formed on the body, the at least two strap assemblies comprising a front strap assembly positioned on the perimeter outer surface of the perimeter portion of the body and a top strap assembly offset vertically from the front strap assembly and positioned on the top outer surface of the top portion of the body, the at least two strap assemblies configured to cooperate to temporarily secure the anesthesia circuit such that the at least one connector and the at least one hose are flush with at least the perimeter outer surface;
    wherein the apparatus is configured to provide protection of at least the eyes of the patient while simultaneously being configured to secure the anesthesia circuit in a low-profile configuration with the at least one connector and the at least one hose snugged down onto the body via the at least two strap assemblies and thus with minimal interference with an oral or facial surgical site; and
    wherein the front strap assembly overlays the pad.

2. The apparatus of claim 1 wherein the pad is removably engaged with the perimeter portion.

3. The apparatus of claim 2 further comprising the pocket formed on a perimeter inner surface of the perimeter portion and configured for removable receipt of the pad.

4. The apparatus of claim 3 wherein the pocket is formed by a panel affixed to the perimeter inner surface along opposite substantially vertical side seams and further along a bottom seam offset from a lower perimeter edge of the perimeter portion of the body so as to define a pocket opening toward the top portion of the body for the removable receipt of the pad.

5. The apparatus of claim 1 wherein a lower perimeter edge of the perimeter portion defines the opening in the body opposite the top portion, and the top portion defines an apex of the body, whereby a distance across the opening defines a nominal width of the body and a distance from the opening to the apex defines a nominal height of the body.

6. The apparatus of claim 5 wherein the nominal height is at least seventy-five percent (75%) of the nominal width.

7. The apparatus of claim 5 wherein the nominal height is at least seven inches (7 in.).

8. The apparatus of claim 1 wherein the pad is formed having opposite side edges, a bottom edge, and a top edge, wherein a distance between the opposite side edges is in the range of four to six inches (4-6 in.) and the distance between the bottom and the top edge is at least five inches (5 in.).

9. The apparatus of claim 1 wherein the front strap assembly comprises a front first strap portion affixed at one end to the perimeter outer surface and a front second strap portion affixed to the perimeter outer surface along a length of the front second strap portion, wherein the front second strap portion is substantially parallel to and offset from a lower perimeter edge of the perimeter portion and adjacent to and substantially aligned with the front first strap portion, whereby the front first strap portion is selectively and temporarily engageable with the front second strap portion, the front strap assembly being configured to selectively secure one of the at least one connector or the at least one hose of the anesthesia circuit between the front first strap portion and the front second strap portion and flush with the perimeter outer surface of the perimeter portion of the body.

10. The apparatus of claim 9 wherein the top strap assembly comprises a top first strap portion affixed at one end to the top outer surface and a top second strap portion affixed to the top outer surface along a length of the top second strap portion, wherein the top second strap portion is offset from the front second strap portion and adjacent to and substantially aligned with the top first strap portion, whereby the top first strap portion is selectively and temporarily engageable with the top second strap portion, the top strap assembly being configured to selectively secure one of the at least one connector or the at least one hose of the anesthesia circuit between the top first strap portion and the top second strap portion flush with the top outer surface of the top portion of the body, wherein the front strap assembly and the top strap assembly are configured to snug down the anesthesia circuit along the perimeter outer surface of the perimeter portion of the body and the top outer surface of the top portion of the body.

11. The apparatus of claim 1, wherein the at least two strap assemblies further comprise at least one side strap assembly positioned on the perimeter outer surface of the perimeter portion of the body, wherein the at least one side strap assembly is offset circumferentially to the front strap assembly and wherein the at least one side strap is oriented at an angle relative to a direction along which the front strap assembly extends.

12. The apparatus of claim 11, wherein the at least one side strap assembly extends in a direction that is substantially perpendicular to a direction the front strap assembly extends along.

13. The apparatus of claim 11 wherein the at least one side strap assembly comprises a first side strap assembly and a second side strap assembly positioned on opposite sides of the body.

14. The apparatus of claim 11 wherein the at least one side strap assembly comprises a side first strap portion affixed at one end to the perimeter outer surface and a side second strap portion affixed to the perimeter outer surface along a length of the side second strap portion, wherein the side second strap portion is adjacent to and substantially aligned with the side first strap portion, whereby the side first strap portion is selectively and temporarily engageable with the side second strap portion, the at least one side strap assembly being configured to selectively secure the at least one hose of the anesthesia circuit between the side first strap portion and the side second strap portion flush with the perimeter outer surface of the perimeter portion of the body wherein the front strap assembly and the at least one side strap assembly are configured to snug down the anesthesia circuit along the perimeter outer surface of the perimeter portion of the body.

15. The apparatus of claim 1 wherein the perimeter portion comprises opposite breathable side inserts.

16. The apparatus of claim 1 wherein:
    each of the at least two strap assemblies comprise a first strap portion affixed at one end to the body and a second strap portion affixed along a length of the second strap portion to the body, wherein the second strap portion is substantially aligned with the first strap portion; and
    the first strap portion comprises a first fastener portion and the second strap portion comprises a second fastener portion, the first fastener portion and the second fastener portion configured for selective engagement in temporarily securing the first strap portion relative to the second strap portion.

17. The apparatus of claim 1 wherein the pad is integral with the perimeter portion.

18. The apparatus of claim 1 wherein the body is of unitary construction.

19. A combination anesthesia circuit holder and patient protection device apparatus configured to be worn on a head of a patient so as to cover at least the patient's eyes and further configured to temporarily secure an anesthesia circuit during an oral or facial surgical procedure, the anesthesia circuit comprising at least one connector and at least one hose, the apparatus comprising:
    a body having a circumferentially continuous perimeter portion defining an opening configured for receipt of the head of the patient and the body further having a top portion integral with the perimeter portion, the perimeter portion having a perimeter outer surface and the top portion having a top outer surface;
    a single pad positioned at the perimeter portion of the body and extending from the perimeter portion towards the top portion of the body such that the pad is configured for being positioned over at least the eyes of the patient when the body is positioned on the head of the patient, wherein the pad is located entirely within a front half of the body; and
    at least three strap assemblies formed on the body, the at least three strap assemblies comprising a front strap assembly positioned on the perimeter outer surface of the perimeter portion of the body, at least one side strap assembly positioned on the perimeter outer surface of the perimeter portion of the body offset circumferentially from the front strap assembly and oriented at an angle with respect to a direction along which the front strap assembly extends, and a top strap assembly offset vertically from the front strap assembly and positioned on the top outer surface of the top portion of the body, the at least three strap assemblies configured to cooperate to temporarily secure the anesthesia circuit such that the at least one connector and the at least one hose are flush with one or more of the perimeter outer surface and the top outer surface;
    wherein the apparatus is configured to provide protection of at least the eyes of the patient while simultaneously being configured to secure the anesthesia circuit in a low-profile configuration with the at least one connector and the at least one hose snugged down onto the body via two of the at least three strap assemblies and thus with minimal interference with an oral or facial surgical site, whereby the front strap assembly and the top strap assembly are configured to snug down the anesthesia circuit along the perimeter outer surface of the perimeter portion of the body and the top outer surface of the top portion of the body, and the front strap assembly and the at least one side strap assembly are configured to snug down the anesthesia circuit along the perimeter outer surface of the perimeter portion of the body.

* * * * *